US012077769B2

(12) United States Patent
Xu et al.

(10) Patent No.: US 12,077,769 B2
(45) Date of Patent: Sep. 3, 2024

(54) ZMWAK-RLK PROTEIN RELATED TO GRAY LEAF SPOT RESISTANCE, AND ENCODING GENE AND APPLICATION THEREOF

(71) Applicant: CHINA AGRICULTURAL UNIVERSITY, Beijing (CN)

(72) Inventors: Mingliang Xu, Beijing (CN); Tao Zhong, Beijing (CN); Xingming Fan, Beijing (CN); Mang Zhu, Beijing (CN); Yan Zhang, Beijing (CN); Ling Xu, Beijing (CN); Li Liu, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 17/433,159

(22) PCT Filed: Feb. 24, 2020

(86) PCT No.: PCT/CN2020/076320

§ 371 (c)(1),
(2) Date: Aug. 23, 2021

(87) PCT Pub. No.: WO2020/173403

PCT Pub. Date: Sep. 3, 2020

(65) Prior Publication Data

US 2022/0177907 A1 Jun. 9, 2022

(30) Foreign Application Priority Data

Feb. 26, 2019 (CN) ......................... 201910140479.1

(51) Int. Cl.
*C12N 15/82* (2006.01)

(52) U.S. Cl.
CPC ................................ *C12N 15/8282* (2013.01)

(58) Field of Classification Search
None
See application file for complete search history.

(56) References Cited

U.S. PATENT DOCUMENTS

2015/0315605 A1* 11/2015 Li ......................... C12N 15/90 800/278
2017/0114356 A1 4/2017 Li et al.

FOREIGN PATENT DOCUMENTS

| | | |
|---|---|---|
| CN | 103987848 A | 8/2014 |
| CN | 104341494 A | 2/2015 |
| CN | 105859860 A | 8/2016 |
| CN | 106701972 A | 5/2017 |
| CN | 109609676 A | 4/2019 |
| CN | 109705200 | 5/2019 |
| WO | 2018/013323 A1 | 1/2018 |

OTHER PUBLICATIONS

Wilson, R. Accession No. AC200186, Sep. 13, 2014.*

PCT Search Report prepared for PCT/CN2020/076320, completed May 12, 2020.

Zhang et al., “QTL mapping of resistance to gray leaf spot in maize”. Theoretical and Applied Genetics, 2012, vol. 125, No. 8, pp. 1797-1808.

Zhang et al., “A retrotransposon in an HKT1 family sodium transporter causes variation of leaf Na+ exclusion and salt tolerance in malze”, New Phytologist, 2018, vol. 217, No. 3, pp. 1161-1176.

Everett et al. “Biochemical markers of embryogenesis in tissue cultures of the maize Inbred 873”, Plant Science, 1985, vol. 41, No. 2, pp. 133-140.

Llu et al. “First Report of Gray Leaf Spot of Maize Caused by Cercospora zeina in China”, Plant Disease, 2013, vol. 97, No. 12, p. 1656.

Zhu et al. “Pyramiding of nine transgenes in maize generates high-level resistance against necrotrophic maize pathogens”, Theoretical and Applied Genetics, 2018, vol. 131, No. 10, pp. 2145-2156.

Qin et al. “ZmHAK5 and ZmHAK1 function in K+ uptake and distribution in maize under low K+ conditions”, Journal of Integrative Plant Biology, 2019, vol. 61, Issue 6, pp. 691-705.

Written Opinion Issued in PCT/CN2020/076320 mailed May 28, 2020. With English Translation.

NCBI, “*Zea mays* rust resistance kinase Lr10 (LOC103634752), transcript variant X1, mRNA”, NCBI Reference Sequence: XM_008657340.2, May 12, 2020.

Xu et al., “High-resolution mapping and characterization of qRgls2, a major quantitative trait locus involved in maize resistance to gray leaf spot”, BMC Plant Biology, 2014, vol. 14, No. 1, p. 230, 10 pages.

Zhongtao, “Cloning and resistance of mechanism of genes for gray leaf spot and stalk rot resistance in maize”, Chinese Doctoral Dissertations Full-Text Database, Agricultural Science and Technology, 2019(2): D046-21. With English-language Abstract.

(Continued)

*Primary Examiner* — Medina A Ibrahim

(74) *Attorney, Agent, or Firm* — Troutman Pepper Hamilton Sanders LLP

(57) ABSTRACT

The present invention discloses a ZmWAK-RLK protein related to gray leaf spot resistance, and an encoding gene and application thereof. The present invention sets forth a protein obtained from a maize inbred line Y32, named ZmWAK-RLK, and being the protein shown in sequence 1 of the sequence listing. A nucleic acid molecule for encoding the ZmWAK-RLK protein is likewise considered to be within the scope of protection of the present invention. The present invention likewise sets forth a method for preparing a transgenic plant, comprising the following step: introducing said nucleic acid molecule into a starting plant, thus obtaining a transgenic plant having enhanced resistance to gray leaf spot. The present invention additionally sets forth a plant breeding method, comprising the following step: increasing the content and/or activity of the ZmWAK-RLK protein in a plant of interest, thus increasing the gray leaf spot resistance of the plant of interest. The present invention has great value when applied to the breeding of maize resistant to gray leaf spot.

15 Claims, 4 Drawing Sheets

Figure 1:
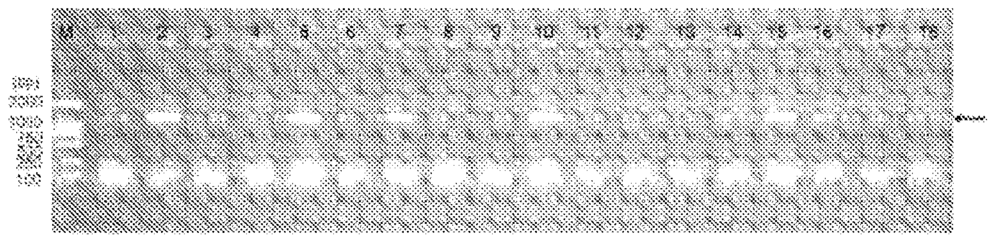

Specification includes a Sequence Listing.

(56) References Cited

OTHER PUBLICATIONS

Sun et al., "Extensive intraspecific gene order and gene structural variations between Mo17 and other maize genomes", Nature Genetics, vol. 50, 2018, pp. 1289-1295.

Genbank, Jun. 4, 2018 PWZ09400.1, Rust resistance kinase Lr10 [*Zea mays*].

Cui et al., "QTL Mapping for Gray Leaf Spot Resistance in Maize Based on Bulk Sequencing", Current Biotechnology, 2018, vol. 8, No. 4, pp. 317-323. With English Abstract.

* cited by examiner non-transgenic plant, transgenic plant

SEQUENCE LISTING

<160> NUMBER OF SEQ ID NOS: 19

<210> SEQ ID NO 1
<211> LENGTH: 665
<212> TYPE: PRT
<213> ORGANISM: Zea mays L.

<400> SEQUENCE: 1

Met Ala Thr Met Ser Ala Ala Ser His Arg Cys Cys Ala Ser Ser Leu
1 5 10 15

Arg Ala Leu Thr Val Leu Phe Val Leu Ala Ala Leu Val Ser Asp Val
20 25 30

Gly Gly Arg His His His His Val Cys Pro Pro Tyr Phe Ser Cys Gly
35 40 45

Gly Phe Ser Asn Ile Ser Tyr Pro Phe Arg Arg Gln Gly Asp Pro Ser
50 55 60

Gly Cys Gly Val Gln Ser Tyr Glu Leu Val Cys Thr Asp Thr Asp Ala
65 70 75 80

Thr Ile Arg Ile Gly Ser Gly Thr Tyr Thr Val Leu Ser Ile Asn Ser
85 90 95

Thr Tyr Ser Tyr Phe Trp Val Val Asp Ala Asp Leu Asp Ile Gln Ser
100 105 110

Ser Cys Pro Leu Pro Trp Trp Asp His His Gly Glu Thr Ser Thr Ala
115 120 125

Asn Ser Tyr Arg Arg Arg Thr Glu Phe Arg Pro Tyr Phe Leu Tyr Pro
130 135 140

Asn Ser Met Ser Ile Ile Phe Val Asn Cys Ser Lys Pro Ile Glu Asn
145 150 155 160

Asn Asp Ile Tyr Glu Pro Val Pro Cys Leu Ser Asn Ser Ser Phe Ile
165 170 175

Tyr Leu Leu Thr His Tyr Ser Tyr Gly Tyr Ala Leu Ala Glu Ile Leu
180 185 190

Glu Pro Ser Cys Gly Tyr Leu Ala Met Ile Tyr Leu Gly Gly Pro Gly
195 200 205

Ile Pro Val Pro Lys Asn Thr Ser Tyr Pro Asp Val Val Lys Leu Met
210 215 220

Arg Asn Gly Phe Gly Leu Arg Phe Pro Ser Ser Ile Gly Asp Arg Gly
225 230 235 240

Ile Arg Glu Cys Phe Ala Glu Ser Val Arg Asn Phe Leu Lys Glu Pro
245 250 255

```
Arg Lys Tyr Gln Ile Val Asp Ile Leu Met Val Glu Glu Leu Trp Ser
            260                 265                 270

Cys Phe Leu Asp Gln His Gly Ser Thr Asn Asn Val Val Thr Ser Val
        275                 280                 285

Ile Ile Asp Ile Ile Lys Thr Ile Pro Ile Cys Met Trp Leu Leu Lys
    290                 295                 300

Ser Thr His Val Phe Cys Arg Leu Val Leu Met Pro Leu Ala Val Phe
305                 310                 315                 320

Val Phe Leu Ala His Lys Tyr Trp Lys Ala Arg Ile Thr Ile Asp Ala
                325                 330                 335

Val Glu Lys Phe Leu Arg Met Gln Gln Met Leu Val Pro Met Arg Tyr
            340                 345                 350

Ala Tyr Thr Asn Ile Ile Ala Ile Thr Gly His Phe Arg Glu Lys Leu
        355                 360                 365

Gly Gln Gly Gly Tyr Gly Ser Val Tyr Lys Gly Val Leu Gln Pro Gly
    370                 375                 380

Glu Val His Val Ala Val Lys Met Leu Gly Asn Ser Asn Cys Asn Gly
385                 390                 395                 400

Glu Glu Phe Ile Ser Glu Val Ala Thr Ile Gly Lys Ile His His Phe
                405                 410                 415

Asn Val Val Arg Leu Ile Gly Phe Cys Ser Glu Glu Asn Arg Arg Ala
            420                 425                 430

Leu Ile Tyr Glu Phe Met Pro His Gly Ser Leu Asp Lys Tyr Ile Phe
        435                 440                 445

Ser Ser Glu Lys Ser Phe Ser Trp Asp Lys Leu Asn Glu Ile Ala Leu
    450                 455                 460

Gly Ile Ala Arg Gly Leu Asn Tyr Leu His His Gly Cys Asp Met Gln
465                 470                 475                 480

Ile Val His Phe Asp Ile Lys Pro His Asn Ile Leu Leu Asp Ser Asn
                485                 490                 495

Phe Val Pro Lys Val Ala Asp Phe Gly Leu Ala Lys Leu Phe Pro Arg
            500                 505                 510

Asp Asp Ser Phe Val Pro Leu Ser Ala Thr Arg Gly Thr Ile Gly Tyr
        515                 520                 525

Ile Ala Pro Glu Met Val Ser Arg Ser Phe Gly Val Ile Ser Ser Lys
    530                 535                 540

Ser Asp Val Tyr Ser Phe Gly Met Leu Leu Leu Glu Met Thr Gly Gly
545                 550                 555                 560

Arg Arg Asn Ala Asp Pro Tyr Ala Gly Ser Ser Ser Gln Ala Tyr Tyr
                565                 570                 575

Pro Ser Leu Val Tyr Ser Gln Leu Ser Gln Gly Asp Leu Gly Glu Ile
            580                 585                 590

Ser Asp Gly Val Asp Met His Glu Leu Glu Lys Lys Leu Cys Ile Ile
        595                 600                 605

Gly Leu Trp Cys Ile Gln Met Lys Pro Gln Asp Arg Pro Thr Met Ser
    610                 615                 620

Asp Val Ile Glu Met Leu Glu Val Gly Val Asp Gly Ile Gln Met Pro
625                 630                 635                 640

Pro Arg Pro Phe Phe Cys Asp Asp Glu Gly Asp Ser Ser Tyr Ser Ala
                645                 650                 655

Ile Ser Glu Ser Asp Thr Ile Glu Glu
            660                 665
```

<210> SEQ ID NO 2
<211> LENGTH: 2238
<212> TYPE: DNA
<213> ORGANISM: Zea mays L.

<400> SEQUENCE: 2
ggcaagaagg tccacgaatc acgcgagcca atcagtggcg tgcagtggcg actgcaaaga 60
taagtgggta gaaacaagag tcacccatgg cgacgatgtc tgcagcgtct catcgctgct 120
gtgcttcttc cttgagagct ttaacggtgt tatttgtgtt ggcagctctt gtttcagatg 180
ttggcgggcg acatcatcat catgtttgtc ctccttattt ctcctgcggt ggttttagca 240
atatatcgta tccattccgt cggcaaggtg atccatcggg gtgcggtgtc caatcgtatg 300
agctggtttg cacggataca gacgctacca ttcgcatcgg cagtggaacg tataccgtgc 360
ttagcatcaa ctccacctat tcttacttct gggtcgttga tgccgacctg gacatccaga 420
gcagttgccc ccttccctgg tgggatcacc atggtgagac cagtactgcc aactcatatc 480
gtaggaggac tgagttcagg ccttatttcc tttatccgaa ttcgatgtcg attatctttg 540
tgaattgctc gaagccaata gagaacaatg atatatatga gccggtgcct tgcttgagca 600
attcttcttt catctacttg ctaactcact actcgtatgg ctatgctctt gctgagattc 660
tggagccctc atgcggttac ctagccatga tttatttggg tggtccaggc ataccggtgc 720
ccaagaatac aagctatcca gatgttgtta agttaatgag gaatggattt ggccttagat 780
ttccttcttc gattggtgac cgcggcatca gagaatgttt cgcagagtct gtgcgtaatt 840
tccttaaaga gccaagaaag tatcagattg tggacattct aatggtcgag gaattatggt 900
cttgttttct cgatcaacat ggatcaacta ataatgttgt cacttctgtt atcatcgaca 960
ttatcaaaac aataccaata tgtatgtggc ttctgaaatc tacacatgtt ttttgcaggc 1020
ttgtattgat gccgctagca gtatttgtct tcctagccca taaatactgg aaagcaagga 1080
ttacaataga tgcagtcgag aagttcctgc ggatgcagca gatgctcgtt ccgatgagat 1140
atgcatacac aaacatcatt gctatcaccg gtcattttag agaaaagctc ggacaaggag 1200
gctacggttc tgtatacaag gggtgctac agccaggtga agtacatgtt gctgtcaaga 1260
tgttaggcaa ctccaactgt aatggagaag agttcatcag tgaggtcgcc accattggca 1320
agatccacca tttcaatgtt gtgcgcctca ttgggttttg ctccgaggaa aatagaaggg 1380
cacttatcta cgagttcatg ccccatggat ctctcgataa gtacatcttc tcgtcggaga 1440
agagtttctc atgggacaaa ctcaatgaga tcgctctggg cattgctaga ggtctcaact 1500
acctacatca cgggtgcgat atgcaaattg tacacttcga catcaagcca cacaacatcc 1560
ttcttgacag caactttgtt ccaaaagttg ctgattttgg gcttgccaaa ctgttcccaa 1620
gagacgacag tttcgtgcca ctgagcgcta cgcggggaac gataggctat atagctccag 1680
agatggtatc tcgaagcttt ggtgtcatct ctagcaaatc tgatgtgtat agctttggaa 1740
tgctactgtt ggagatgacg ggcgggcgaa ggaacgcaga tccttatgca ggaagctcca 1800
gtcaagcata ctacccatcc ttggtgtaca gccagctaag ccaaggagat ttgggcgaga 1860
tcagtgacgg tgttgatatg cacgagttag agaagaagct atgtatcatt ggactttggt 1920
gcatccagat gaagccgcaa gatcgaccga cgatgagcga cgtcatagag atgcttgaag 1980
ttggtgtcga tggcatccaa atgcctccaa ggccattctt ttgtgatgac gagggtgata 2040
gttcttactc tgcaatctct gaatcggata caatagaaga gtagtagtag taaaatacac 2100
ttgtgtatat ttgatcttaa tgtattttag actactaaga atgcaaggtt gtcataagct 2160

```
aaggtactgg ttgtatactt ttattgagag tgtggtaatg tgttttcatt taaaatacct   2220

caatgaacct tttttatc                                                 2238


<210> SEQ ID NO 3
<211> LENGTH: 2213
<212> TYPE: DNA
<213> ORGANISM: Zea mays L.

<400> SEQUENCE: 3

atggcgacga tgtctgcagc gtctcatcgc tgctgtgctt cttccttgag agctttaacg     60

gtgttatttg tgttggcagc tcttgtttca gatgttggcg ggcgacatca tcatcatgtt    120

tgtcctcctt atttctcctg cggtggtttt agcaatatat cgtatccatt ccgtcggcaa    180

ggtgatccat cggggtgcgg tgtccaatcg tatgagctgg tttgcacgga tacagacgct    240

accattcgca tcggcagtgg aacgtatacc gtgcttagca tcaactccac ctattcttac    300

ttctgggtcg ttgatgccga cctggacatc cagagcagtt gcccccttcc ctggtgggat    360

caccatggtg agaccagtac tgccaactca tatcgtagga ggactgagtt caggccttat    420

ttcctttatc cgaattcgat gtcgattatc tttgtgaatt gctcgaagcc aatagagaac    480

aatgatatat atgagccggt gccttgcttg agcaattctt ctttcatcta cttgctaact    540

cactactcgt atggctatgc tcttgctgag attctggagc cctcatgcgg ttacctagcc    600

atgatttatt tgggtggtcc aggcataccg gtgcccaaga atacaagcta tccagatgtt    660

gttaagttaa tgaggaatgg atttggcctt agatttcctt cttcgattgg tgaccgcggc    720

atcagagaat gtttcgcaga gtctgtgcgg tatctgatca tcctatccta ttttcctcct    780

atgcatgact ttgtcatctg aaaaccgtcc gttgcattcc cttcgtaatt cttttatatg    840

ctatggcatg gtcttgcagt aatttcctta aagagccaag aaagtatcag attgtggaca    900

ttctaatggt cgaggaatta tggtcttgtt ttctcgatca acatggatca actaataatg    960

ttgtcacttc tgttatcatc gacattatca aaacaatacc aatatgtatg tggcttctga   1020

aatctacaca tggtactctc tccggctatc atcatttgtt gaataaacat cgtatgtttt   1080

gtggcttctg ttttttttta attcttcatg tttacaacct tggatttttt tcggcagttt   1140

tttgcaggct tgtattgatg ccgctagcag tatttgtctt cctagcccat aaatactgga   1200

aagcaaggat tacaatagat gcagtcgaga agttcctgcg gatgcagcag atgctcgttc   1260

cgatgagata tgcatacaca aacatcattg ctatcaccgg tcattttaga gaaaagctcg   1320

gacaaggagg ctacggttct gtatacaagg gggtgctaca gccaggtgaa gtacatgttg   1380

ctgtcaagat gttaggcaac tccaactgta atggagaaga gttcatcagt gaggtcgcca   1440

ccattggcaa gatccaccat ttcaatgttg tgcgcctcat tgggttttgc tccgaggaaa   1500

atagaagggc acttatctac gagttcatgc cccatggatc tctcgataag tacatcttct   1560

cgtcggagaa gagtttctca tgggacaaac tcaatgagat cgctctgggc attgctagag   1620

gtctcaacta cctacatcac gggtgcgata tgcaaattgt acacttcgac atcaagccac   1680

acaacatcct tcttgacagc aactttgttc caaaagttgc tgattttggg cttgccaaac   1740

tgttcccaag agacgacagt ttcgtgccac tgagcgctac gcggggaacg ataggctata   1800

tagctccaga gatggtatct cgaagctttg gtgtcatctc tagcaaatct gatgtgtata   1860

gctttggaat gctactgttg gagatgacgg gcgggcgaag gaacgcagat ccttatgcag   1920

gaagctccag tcaagcatac tacccatcct tggtgtacag ccagctaagc caaggagatt   1980
```

```
tgggcgagat cagtgacggt gttgatatgc acgagttaga gaagaagcta tgtatcattg   2040

gactttggtg catccagatg aagccgcaag atcgaccgac gatgagcgac gtcatagaga   2100

tgcttgaagt tggtgtcgat ggcatccaaa tgcctccaag gccattcttt tgtgatgacg   2160

agggtgatag ttcttactct gcaatctctg aatcggatac aatagaagag tag          2213
```

```
<210> SEQ ID NO 4
<211> LENGTH: 7238
<212> TYPE: DNA
<213> ORGANISM: Zea mays L.

<400> SEQUENCE: 4

tccactcgtg atccctgatc accaaaccag cccttagcca atcacctgca acttgatctt     60

cgcaaaagct agttgttagt cgattaggtt cgcctttgac tctcatttgt taatgatagt    120

tgggtcctgt ctgactagca gatagtctac aaaatttttg atcatcttca gtgtatccca    180

aatagtaggg tgaagatggg gagtgtcact catttatttg cgttttatgc cttatggata    240

tgtaaagtgt gtataaaatg gtttagagag aattaaattg tttattttgc taatcatttt    300

tctggtgtcg ggtaccaaaa tgcacatgtt ttgttgtaca tgtaagttct ttatgactga    360

tgtgtagtca tcactacgag tgcttgaaat agtgttggga gctaggagga agtctatgta    420

ttctgtagca gtagcattat gcgacatcat taccataatt acaaataaac taatcgtagc    480

cacgatgttc aatacattaa ctttttggta acaaataaat gtaaaatggg gaatgagagg    540

ttgcaatgtc tactgatttc tacgattttt cttatcagtg agtatgttgg tagcttcttt    600

ttctctttct aagtataaca tctttgtcgt tttaaattca tgagaatgat taaatataat    660

aggggaactt tgaatatgtt catattctta tctaattgtg caagttctat caatcatata    720

aattctaaaa taggcatgtc ttataacttt gattcttttg aacaatttag tttatggacc    780

aactatgttt gtatatgaac agatgacaga catagcaaaa cttgtctaca atcttatata    840

tcttttaagg tacataaata tctaatttta gtgatgctaa caaaagtata gaataacaat    900

tacggggcgt ttggatccct tcattttaga agaattagaa ttcactcaat aaagtgactt    960

atttagttta gaatttgaca ttccaccact tttcaaagtt aggtataagc ctatctcaaa   1020

tttatgtggt ggaggatgag aaatgatttt attcattagt agaatttgtt tctactctgt   1080

aacttacatg acactcttcg tctcactcct ctatagtaaa aatatagcac ataaatatct   1140

ccaacatctt gctaataata gtatacaaat atattttgca taaaacagaa ttagcttaat   1200

tgatatatgt caaaattact attattagaa tggaattcaa ttcgaatgat ccaaacgagg   1260

cgttagtgtt tttatcatat taattccgta gcaacgcacg agtatataac tagtctttaa   1320

taaggtgtat acaaactata gattgttcaa acaatttcta tcattatgct ctagctataa   1380

tttaactttg caaaacacac cttggtcata ataattttat attatcatta atcaccgaaa   1440

aataggaggg tctagatgct ttcaacattc ataggaaagc atctcatcta atgtttcata   1500

tactgtatat attgataaga tgaaaagata aacacgaggc ggaccataca ctttatcatt   1560

tagttccaaa ttaactgaca ctaaagttct tttcataaca gggactgaag agcatttctc   1620

tactagtagt ggagcagatc caaatagact gaaatatgcc gataaatcta ccaagtatat   1680

catatgagta tacttcggtt taataagaca ctgactgagc aaggatgccg gccgcttcaa   1740

ggtttgcact tgaaagtagc actccagatg atattggtta ctgcattgaa ataccttttt   1800

taattacatt ttattccgta tatatccaag tttatactgg tttgcggtgg taaaattatc   1860

tcttcatctc cggtcccata tccccatcga aggccatttg caaaccagaa aaagacgcaa   1920
```

-continued

```
aagaatgact accaagtcag cggcatcaca attatgtgga ccagtcatgt gcgattttgt   1980
tccacaaata cagcgaagat gctgaggctg tgaccccggg tgactcttgt ttctacccac   2040
ttatctttgc agtcgccact gcacgccact gattggctcg cgtgattcgt ggaccttctt   2100
gccatggcga cgatgtctgc agcgtctcat cgctgctgtg cttcttcctt gagagcttta   2160
acggtgttat ttgtgttggc agctcttgtt tcagatgttg gcgggcgaca tcatcatcat   2220
gtttgtcctc cttatttctc ctgcggtggt tttagcaata tatcgtatcc attccgtcgg   2280
caaggtgatc catcggggtg cggtgtccaa tcgtatgagc tggtttgcac ggatacagac   2340
gctaccattc gcatcggcag tggaacgtat accgtgctta gcatcaactc cacctattct   2400
tacttctggg tcgttgatgc cgacctggac atccagagca gttgccccct tccctggtgg   2460
gatcaccatg gtgagaccag tactgccaac tcatatcgta ggaggactga gttcaggcct   2520
tatttccttt atccgaattc gatgtcgatt atctttgtga attgctcgaa gccaatagag   2580
aacaatgata tatatgagcc ggtgccttgc ttgagcaatt cttctttcat ctacttgcta   2640
actcactact cgtatggcta tgctcttgct gagattctgg agccctcatg cggttaccta   2700
gccatgattt atttgggtgg tccaggcata ccggtgccca agaatacaag ctatccagat   2760
gttgttaagt taatgaggaa tggatttggc cttagatttc cttcttcgat tggtgaccgc   2820
ggcatcagag aatgtttcgc agagtctgtg cggtatctga tcatcctatc ctattttcct   2880
cctatgcatg actttgtcat ctgaaaaccg tccgttgcat tcccttcgta attcttttat   2940
atgctatggc atggtcttgc agtaatttcc ttaaagagcc aagaaagtat cagattgtgg   3000
acattctaat ggtcgaggaa ttatggtctt gttttctcga tcaacatgga tcaactaata   3060
atgttgtcac ttctgttatc atcgacatta tcaaaacaat accaatatgt atgtggcttc   3120
tgaaatctac acatggtact ctctccggct atcatcattt gttgaataaa catcgtatgt   3180
tttgtggctt ctgttttttt ttaattcttc atgtttacaa ccttggattt ttttcggcag   3240
ttttttgcag gcttgtattg atgccgctag cagtatttgt cttcctagcc cataaatact   3300
ggaaagcaag gattacaata gatgcagtcg agaagttcct gcggatgcag cagatgctcg   3360
ttccgatgag atatgcatac acaaacatca ttgctatcac cggtcatttt agagaaaagc   3420
tcggacaagg aggctacggt tctgtataca agggggtgct acagccaggt gaagtacatg   3480
ttgctgtcaa gatgttaggc aactccaact gtaatggaga agagttcatc agtgaggtcg   3540
ccaccattgg caagatccac catttcaatg ttgtgcgcct cattgggttt tgctccgagg   3600
aaaatagaag ggcacttatc tacgagttca tgccccatgg atctctcgat aagtacatct   3660
tctcgtcgga gaagagtttc tcatgggaca aactcaatga gatcgctctg ggcattgcta   3720
gaggtctcaa ctacctacat cacgggtgcg atatgcaaat tgtacacttc gacatcaagc   3780
cacacaacat ccttcttgac agcaactttg ttccaaaagt tgctgatttt gggcttgcca   3840
aactgttccc aagagacgac agtttcgtgc cactgagcgc tacgcgggga acgataggct   3900
atatagctcc agagatggta tctcgaagct ttggtgtcat ctctagcaaa tctgatgtgt   3960
atagctttgg aatgctactg ttggagatga cgggcgggcg aaggaacgca gatccttatg   4020
caggaagctc cagtcaagca tactacccat ccttggtgta cagccagcta agccaaggag   4080
atttgggcga gatcagtgac ggtgttgata tgcacgagtt agagaagaag ctatgtatca   4140
ttggactttg gtgcatccag atgaagccgc aagatcgacc gacgatgagc gacgtcatag   4200
agatgcttga agttggtgtc gatggcatcc aaatgcctcc aaggccattc ttttgtgatg   4260
```

-continued

```
acgagggtga tagttcttac tctgcaatct ctgaatcgga tacaatagaa gagtagtagt   4320
agtaaaatac acttgtgtat atttgatctt aatgtatttt agactactaa gaatgcaagg   4380
ttgtcataag ctaaggtact ggttgtatac ttttattgag agtgtggtaa tgtgttttca   4440
tttaaaatac ctcaatgaac ctttttatc aaaaactcct caagaacatt ttgtttgcca   4500
acaaacatag gatcacggtc ccagccgttg tattcagcta ttgcacaagt ttttaagtta   4560
tgcataacaa attaagtgaa ctagcatatt acccgcgcta gcaccaagat aatatttgac   4620
aatacaaatt aaataaccaa aaggttattc atctcatata atataatgcc catgctaaag   4680
accgctcatg tagaacgcga cattcatttg aaggcattag taccagttgt tgtagaatcg   4740
atattgattc aggcgtcagt accgatttta atgaccacgt cctcatggat ggcaatagta   4800
tagattggtg tctcaaatca atgcaaaagg actctatctg agttagttag gtggtctgag   4860
tgacactcaa attctaaatt ctaagtttga gctcctatga aagcaaattt taggctacgg   4920
ttaaaaattc tcttgtatca ttattcttgt gtattcaact gatgtcatta ttcttatttg   4980
tcttcactat agaatttgca tttcctacac acactaccta tatgatttaa ggttcaggat   5040
cgtaactcaa agtagttgga tttaggatta ttttaacaag aacatccatt tttcatgagc   5100
ttaatattaa acccttttt gttttatatg tttttcattg gaatcatgct aagatagatc   5160
atcgtaaaat agaggagaag ttgaatcatg aactagcatt tagaaaggaa ataagaagat   5220
acatctagct agcacttagg gatactgtca caccaagatt taaggataaa ttcagatgca   5280
cctcatatgt gcgccatgat caagtttcac acatataaat actcaatgta tagtagccaa   5340
tgtcacaagc tttattatat aacgaaaatg acttacaaaa taactggaat aaaataaatc   5400
gaactaacat aactatctcc atgatgtgaa tgttgtgcgc ctcatcgggt tttgctccga   5460
tgaaaatagg agggcactca tatatgagtt catgccccgt ggatccctcg ataggtacat   5520
cttctcgtcg aagaagagtt tctgatggga caaactcaat gagatcgctc tgggcattgc   5580
tagaggtctc aactacctgc gtcacgggtg tgacatgcag attgtacact tcgacatcaa   5640
gccacacaac atccttcttg acaacaactt tgttccaaaa gttgctgatt ttgggctcac   5700
caaactgttc ccaagagatg acagtttcgt gccactaagc gctgtgcagg gaacgatagg   5760
ctatataact acatagatgg tatctccaag ctttggtgtc atctctagca aattcgatgt   5820
gtatagcttt gggatgctac tattggagat ggcgggcgat caaaggaacg cagatcctca   5880
agcaggaagc tccagccaag catactaccc atccttcgtg tacagccagc tgagccaagg   5940
agatgttgat gggatcagtg aaggtgttga tatgcatgag ttagagaaga agttatgtat   6000
catcgggctt tggtgcatct agatgaagcc gcaagataga ccgacgatga gcgaggtcat   6060
agagatgctt gaagctagtg ttgatggcat ccaaatgcct ccaaggccat tcttttgtga   6120
tgacgagggt gacagttctt actctacaat ctctgaactg tatacaatat aagagtagta   6180
gtaataaact gcacttgtgt ttatgcgctc ttaatgtatc atagtattaa gattgcaagg   6240
ttgtcataag ctaaggtact agttgtatac ttttattgag agtgtgataa tgtgatgtca   6300
tctaaaatac ctccatgaac ctttttatc aaaaactcat caagaacatt ttgtttgcct   6360
acaaacagag gaccacggtc ccagacattg tattcttgaa aaggaatgca ctagttttat   6420
gcacgtcaat ccgaaggcta ttacacaact ttcttagtta tgcataataa attaggtaaa   6480
ctagcatatt actcgtgcta acactatgat aatcaaaaga atatattctt tacagctagt   6540
ccaagaaaca caggagattg tatttgggga tagtggcaag agtaaggtgg ttggtattgg   6600
taacattcct atctcaacaa agcagtcact atccaatgtt ctattagttg attccttaag   6660
```

```
ttataacctt ttgtctgttt tacaactttg tgcaatgggt tttgattgtc tttttacaaa   6720
tgtcagtgtg aaaattctta gaagggagca ttcctatgtt gcctttatag gatagctgac   6780
aggcaagctc taccttgttg attttcaaac aagtagagtg tcatctgata cttatttagt   6840
ggcaaagtcc aacaagggtt ggctctagca ttgctggcta gctcatgttg gcatgagaaa   6900
cttgggcaaa cttctaaaga atgatcacat tattggacta acaaatgtta tatttgagaa   6960
cgacagggtt tgtggagctt gccaagcaag aaaacaacat ggagctctcc accatccaaa   7020
gaatgcggtc accaccaaaa aggcctttgg agcttctaca catggtcctt ttcggaccgg   7080
tggcctacct cagtattggt ggtaacaaat atggcttggt tattgttcat gatttttctt   7140
gcttcacttg tgttttttc tttttgggtg acaaaggtga aacccaatag attctaaaga   7200
aggtcatgag gcgagcacaa aatgaatttg agctaaag                           7238
```

```
<210> SEQ ID NO 5
<211> LENGTH: 2115
<212> TYPE: DNA
<213> ORGANISM: Zea mays L.

<400> SEQUENCE: 5
```

```
atgccgatgt ctgattcttc cttgagagct ttaacggtgt tatttgtgtt ggcagctctt     60
gtttcagatg tagaggggcg acatcatcgt catgtctgtc ctcatttctc ctgcggtggt    120
ttaagcaata tatggtatcc atttcgtcgg caaggtgatc catcggggtg cggtgtccaa    180
tcgtatgagc tggtttgcac ggatacagat gctacaattc gcatcggcag tggaacatac    240
aaggtgctta gcatcaactc cacatattct cacttctggg ttgttgatgc caacctggcc    300
gacatccaga gcagttgccc ccttccccgg tgggattacc atgctaggag gaccagtagt    360
aacttacatc gttggaggat tgagttcagc catgattttt ctaattctaa tccgatgtgg    420
gtttacgctg acgcttactt tgattggacc cgtggcaact catatcgtca gaggattgag    480
ttcagccatg atacccagtt ttcttctttg gattattcgg ggtgggctat ctttgtgaat    540
tgttctcagc caatagagaa catatataat aatatatatg atgacgttgt gtatgggccg    600
gtctcttgct tgagcaattc ttcttttatc tacttgttaa ctcactggta tgctggccat    660
gttcctgctg ggagtctgga gccttcatgc ggttacctag ccatgactcc tttgggtggt    720
ccaggcatgc cggtgccctc gaatataggc tatccagatg ttgttaagtt catgaggagt    780
ggatttgccc ttcgatttcc cttttcgtat ggtgataaca tcagagaatg tctcgcagag    840
aatatgcgtg ctttccatga agaaccaaga aatagtacag gcatcaggga acagatcttg    900
gacattctta cattcgagac attatggttt tgtgttattg atcaacttgg atcaagtaat    960
aatgttgtca aatctgttct catcaacatc atcgtcagaa taataccatt tgttctgtgg   1020
ggtctaaaat ctgcacatgt tatttgcagg ttcgtattga tgccgctggc agtatttgtc   1080
ttcctagcct ataaatactg gaaaacacgg ataacaatag atgcagtcga gaagttcctg   1140
cgaatgcagc atatgctcgt tccgatgaga tatgcataca caaacatcat tgcaatcacc   1200
agccatttca gagacaagct cggacaagga ggctacggta ctgtatacaa gggggtgcta   1260
cagccaggtg aagttcatgt tgctattaag atgctaggca actccaactg taacggagac   1320
gagttcatca gtgaggtggc caccattgga aagatccacc atgtcaatgt tgtgcgcctc   1380
attgggtttt gctccgagga aaatatcagg gcacttatct atgagttcat gccccgtgga   1440
tctctcgata agtacatctt ctcgtcggag aagacattct catgggacaa actcaacgag   1500
```

```
atcgctctgg gcattgctag aggtctcaac tacctacatc acgggtgtga tatgcagatt   1560
gtacacttcg acatcaagcc acacaacatc cttcttgaca gcaactttgt tccaaaagtt   1620
gctgattttg ggcttgccaa actgttccca agaggcgaca ctttcgtgcc actgagcgct   1680
atgcggggaa cgataggata tatagctcca gagatggtat ctcgaagctt tggtgtcatc   1740
tctagcaaat ctgatgtgta tagctttgga atgctactgt tggagatgac gggcgggcga   1800
aggaatgcag atcctcatgc aggaagctcc agtcaagcat actacccatc cttggtgtac   1860
agccaactaa gccaaggaga tgtgggcggg atcagtaaag gtgttgatat gcacgagtta   1920
gagaagaagc tatgtatcat tggactttgg tgcatccaga tgaagacgca agatcgacag   1980
acgatgagtg aggtcataga gatgcttgaa gctagtgtcg atggcatcca aatgcctcca   2040
aggccattct tttgtgatga cgagggtgat agttcttact ctgcaatctc tgaattggat   2100
acaatagaag agtag                                                    2115
```

```
<210> SEQ ID NO 6
<211> LENGTH: 1986
<212> TYPE: DNA
<213> ORGANISM: Artificial sequence
<220> FEATURE:
<223> OTHER INFORMATION: Synthetic construct

<400> SEQUENCE: 6

atggcgacga tgtctgcagc gtctcatcgc tgctgtgctt cttccttgag agctttaacg     60
gtgttatttg tgttggcagc tcttgtttca gatgttggcg ggcgacatca tcatcatgtt    120
tgtcctcctt atttctcctg cggtggtttt agcaatatat cgtatccatt ccgtcggcaa    180
ggtgatccat cggggtgcgg tgtccaatcg tatgagctgg tttgcacgga tacagacgct    240
accattcgca tcggcagtgg aacgtatacc gtgcttagca tcaactccac ctattcttac    300
ttctgggtcg ttgatgccga cctggacatc cagagcagtt gcccccttcc ctggtgggat    360
caccatggtg agaccagtac tgccaactca tatcgtagga ggactgagtt caggccttat    420
ttcctttatc cgaattcgat gtcgattatc tttgtgaatt gctcgaagcc aatagagaac    480
aatgatatat atgagccggt gccttgcttg agcaattctt ctttcatcta cttgctaact    540
cactactcgt atggctatgc tcttgctgag attctggagc cctcatgcgg ttacctagcc    600
atgatttatt tgggtggtcc aggcataccg gtgcccaaga atacaagcta tccagatgtt    660
gttaagttaa tgaggaatgg atttggcctt agatttcctt cttcgattgg tgaccgcggc    720
atcagagaat gtttcgcaga gtctgtgcgt aatttcctta aagagccaag aaagtatcag    780
attgtggaca ttctaatggt cgaggaatta tggtcttgtt ttctcgatca acatggatca    840
actaataatg ttgtcacttc tgttatcatc gacattatca aaacaatacc aatatgtatg    900
tggcttctga aatctacaca tgtttttgc aggcttgtat tgatgccgct agcagtattt     960
gtcttcctag ccaaaacacg gataacaata gatgcagtcg agaagttcct gcgaatgcag   1020
catatgctcg ttccgatgag atatgcatac acaaacatca ttgcaatcac cagccatttc   1080
agagacaagc tcggacaagg aggctacggt actgtataca agggggtgct acagccaggt   1140
gaagttcatg ttgctattaa gatgctaggc aactccaact gtaacggaga cgagttcatc   1200
agtgaggtgg ccaccattgg aaagatccac catgtcaatg ttgtgcgcct cattgggttt   1260
tgctccgagg aaaatatcag ggcacttatc tatgagttca tgccccgtgg atctctcgat   1320
aagtacatct tctcgtcgga gaagacattc tcatgggaca aactcaacga gatcgctctg   1380
ggcattgcta gaggtctcaa ctacctacat cacgggtgtg atatgcagat tgtacacttc   1440
```

```
gacatcaagc cacacaacat ccttcttgac agcaactttg ttccaaaagt tgctgatttt   1500

gggcttgcca aactgttccc aagaggcgac actttcgtgc cactgagcgc tatgcgggga   1560

acgataggat atatagctcc agagatggta tctcgaagct ttggtgtcat ctctagcaaa   1620

tctgatgtgt atagctttgg aatgctactg ttggagatga cgggcgggcg aaggaatgca   1680

gatcctcatg caggaagctc cagtcaagca tactacccat ccttggtgta cagccaacta   1740

agccaaggag atgtgggcgg gatcagtaaa ggtgttgata tgcacgagtt agagaagaag   1800

ctatgtatca ttggactttg gtgcatccag atgaagacgc aagatcgaca gacgatgagt   1860

gaggtcatag agatgcttga agctagtgtc gatggcatcc aaatgcctcc aaggccattc   1920

ttttgtgatg acgagggtga tagttcttac tctgcaatct ctgaattgga tacaatagaa   1980

gagtag                                                              1986


<210> SEQ ID NO 7
<211> LENGTH: 661
<212> TYPE: PRT
<213> ORGANISM: Artificial sequence
<220> FEATURE:
<223> OTHER INFORMATION: Synthetic construct

<400> SEQUENCE: 7

Met Ala Thr Met Ser Ala Ala Ser His Arg Cys Cys Ala Ser Ser Leu
1               5                   10                  15

Arg Ala Leu Thr Val Leu Phe Val Leu Ala Ala Leu Val Ser Asp Val
            20                  25                  30

Gly Gly Arg His His His His Val Cys Pro Pro Tyr Phe Ser Cys Gly
        35                  40                  45

Gly Phe Ser Asn Ile Ser Tyr Pro Phe Arg Arg Gln Gly Asp Pro Ser
    50                  55                  60

Gly Cys Gly Val Gln Ser Tyr Glu Leu Val Cys Thr Asp Thr Asp Ala
65                  70                  75                  80

Thr Ile Arg Ile Gly Ser Gly Thr Tyr Thr Val Leu Ser Ile Asn Ser
                85                  90                  95

Thr Tyr Ser Tyr Phe Trp Val Val Asp Ala Asp Leu Asp Ile Gln Ser
            100                 105                 110

Ser Cys Pro Leu Pro Trp Trp Asp His His Gly Glu Thr Ser Thr Ala
        115                 120                 125

Asn Ser Tyr Arg Arg Arg Thr Glu Phe Arg Pro Tyr Phe Leu Tyr Pro
    130                 135                 140

Asn Ser Met Ser Ile Ile Phe Val Asn Cys Ser Lys Pro Ile Glu Asn
145                 150                 155                 160

Asn Asp Ile Tyr Glu Pro Val Pro Cys Leu Ser Asn Ser Ser Phe Ile
                165                 170                 175

Tyr Leu Leu Thr His Tyr Ser Tyr Gly Tyr Ala Leu Ala Glu Ile Leu
            180                 185                 190

Glu Pro Ser Cys Gly Tyr Leu Ala Met Ile Tyr Leu Gly Gly Pro Gly
        195                 200                 205

Ile Pro Val Pro Lys Asn Thr Ser Tyr Pro Asp Val Val Lys Leu Met
    210                 215                 220

Arg Asn Gly Phe Gly Leu Arg Phe Pro Ser Ser Ile Gly Asp Arg Gly
225                 230                 235                 240

Ile Arg Glu Cys Phe Ala Glu Ser Val Arg Asn Phe Leu Lys Glu Pro
                245                 250                 255
```

```
Arg Lys Tyr Gln Ile Val Asp Ile Leu Met Val Glu Glu Leu Trp Ser
            260                 265                 270

Cys Phe Leu Asp Gln His Gly Ser Thr Asn Asn Val Val Thr Ser Val
        275                 280                 285

Ile Ile Asp Ile Ile Lys Thr Ile Pro Ile Cys Met Trp Leu Leu Lys
    290                 295                 300

Ser Thr His Val Phe Cys Arg Leu Val Leu Met Pro Leu Ala Val Phe
305                 310                 315                 320

Val Phe Leu Ala Lys Thr Arg Ile Thr Ile Asp Ala Val Glu Lys Phe
                325                 330                 335

Leu Arg Met Gln His Met Leu Val Pro Met Arg Tyr Ala Tyr Thr Asn
            340                 345                 350

Ile Ile Ala Ile Thr Ser His Phe Arg Asp Lys Leu Gly Gln Gly Gly
        355                 360                 365

Tyr Gly Thr Val Tyr Lys Gly Val Leu Gln Pro Gly Glu Val His Val
    370                 375                 380

Ala Ile Lys Met Leu Gly Asn Ser Asn Cys Asn Gly Asp Glu Phe Ile
385                 390                 395                 400

Ser Glu Val Ala Thr Ile Gly Lys Ile His His Val Asn Val Val Arg
                405                 410                 415

Leu Ile Gly Phe Cys Ser Glu Glu Asn Ile Arg Ala Leu Ile Tyr Glu
            420                 425                 430

Phe Met Pro Arg Gly Ser Leu Asp Lys Tyr Ile Phe Ser Ser Glu Lys
        435                 440                 445

Thr Phe Ser Trp Asp Lys Leu Asn Glu Ile Ala Leu Gly Ile Ala Arg
    450                 455                 460

Gly Leu Asn Tyr Leu His His Gly Cys Asp Met Gln Ile Val His Phe
465                 470                 475                 480

Asp Ile Lys Pro His Asn Ile Leu Leu Asp Ser Asn Phe Val Pro Lys
                485                 490                 495

Val Ala Asp Phe Gly Leu Ala Lys Leu Phe Pro Arg Gly Asp Thr Phe
            500                 505                 510

Val Pro Leu Ser Ala Met Arg Gly Thr Ile Gly Tyr Ile Ala Pro Glu
        515                 520                 525

Met Val Ser Arg Ser Phe Gly Val Ile Ser Ser Lys Ser Asp Val Tyr
    530                 535                 540

Ser Phe Gly Met Leu Leu Leu Glu Met Thr Gly Gly Arg Arg Asn Ala
545                 550                 555                 560

Asp Pro His Ala Gly Ser Ser Ser Gln Ala Tyr Tyr Pro Ser Leu Val
                565                 570                 575

Tyr Ser Gln Leu Ser Gln Gly Asp Val Gly Gly Ile Ser Lys Gly Val
            580                 585                 590

Asp Met His Glu Leu Glu Lys Lys Leu Cys Ile Ile Gly Leu Trp Cys
        595                 600                 605

Ile Gln Met Lys Thr Gln Asp Arg Gln Thr Met Ser Glu Val Ile Glu
    610                 615                 620

Met Leu Glu Ala Ser Val Asp Gly Ile Gln Met Pro Pro Arg Pro Phe
625                 630                 635                 640

Phe Cys Asp Asp Glu Gly Asp Ser Ser Tyr Ser Ala Ile Ser Glu Leu
                645                 650                 655

Asp Thr Ile Glu Glu
            660
```

<210> SEQ ID NO 8
<211> LENGTH: 4
<212> TYPE: PRT
<213> ORGANISM: Artificial Sequence
<220> FEATURE:
<223> OTHER INFORMATION: peptide tag

<400> SEQUENCE: 8

Arg Arg Arg Arg
1

<210> SEQ ID NO 9
<211> LENGTH: 6
<212> TYPE: PRT
<213> ORGANISM: Artificial Sequence
<220> FEATURE:
<223> OTHER INFORMATION: peptide tag

<400> SEQUENCE: 9

His His His His His His
1 5

<210> SEQ ID NO 10
<211> LENGTH: 8
<212> TYPE: PRT
<213> ORGANISM: Artificial Sequence
<220> FEATURE:
<223> OTHER INFORMATION: peptide tag

<400> SEQUENCE: 10

Asp Tyr Lys Asp Asp Asp Asp Lys
1 5

<210> SEQ ID NO 11
<211> LENGTH: 8
<212> TYPE: PRT
<213> ORGANISM: Artificial Sequence
<220> FEATURE:
<223> OTHER INFORMATION: peptide tag

<400> SEQUENCE: 11

Trp Ser His Pro Gln Phe Glu Lys
1 5

<210> SEQ ID NO 12
<211> LENGTH: 10
<212> TYPE: PRT
<213> ORGANISM: Artificial Sequence
<220> FEATURE:
<223> OTHER INFORMATION: peptide tag

<400> SEQUENCE: 12

Glu Gln Lys Leu Ile Ser Glu Glu Asp Leu
1 5 10

<210> SEQ ID NO 13
<211> LENGTH: 9
<212> TYPE: PRT
<213> ORGANISM: Artificial Sequence
<220> FEATURE:
<223> OTHER INFORMATION: peptide tag

<400> SEQUENCE: 13

Tyr Pro Tyr Asp Val Pro Asp Tyr Ala
1 5

<210> SEQ ID NO 14

```
<211> LENGTH: 22
<212> TYPE: DNA
<213> ORGANISM: Artificial Sequence
<220> FEATURE:
<223> OTHER INFORMATION: PCR primer

<400> SEQUENCE: 14

cgaggaggtt tcccgatatt ac                                            22


<210> SEQ ID NO 15
<211> LENGTH: 22
<212> TYPE: DNA
<213> ORGANISM: Artificial Sequence
<220> FEATURE:
<223> OTHER INFORMATION: PCR primer

<400> SEQUENCE: 15

cacgtcaatc cgaaggctat ta                                            22


<210> SEQ ID NO 16
<211> LENGTH: 22
<212> TYPE: DNA
<213> ORGANISM: Artificial Sequence
<220> FEATURE:
<223> OTHER INFORMATION: PCT primer

<400> SEQUENCE: 16

ttttagccct gccttcatac gc                                            22


<210> SEQ ID NO 17
<211> LENGTH: 23
<212> TYPE: DNA
<213> ORGANISM: Artificial Sequence
<220> FEATURE:
<223> OTHER INFORMATION: PCR primer

<400> SEQUENCE: 17

cgacatcgaa ttcggataaa gga                                           23


<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18

ggtggacggc gaggtcgccg                                               20


<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19

tcggtgacgg gcaggaccgg                                               20
```

ZMWAK-RLK PROTEIN RELATED TO GRAY LEAF SPOT RESISTANCE, AND ENCODING GENE AND APPLICATION THEREOF

CROSS-REFERENCE TO RELATED APPLICATIONS

This application is a national stage entry under 35 USC § 371 of PCT International Application Number PCT/CN2020/076320, filed Feb. 24, 2020, which claims priority to Chinese Patent Application Number 201910140479.1 filed Feb. 26, 2019, the entire disclosures of which are incorporated herein by reference.

INCORPORATION BY REFERENCES OF MATERIAL SUBMITTED ELECTRONICALLY

Incorporated by reference in its entirety is a computer-readable nucleotide/amino acid sequence listing submitted concurrently herewith and identified as follows: 33 kilobytes ACII (Text) file named "20762082_ST25.txt," created on Dec. 28, 2021.

TECHNICAL FIELD

The present invention belongs to the field of biotechnology, and specifically relates to a ZmWAK-RLK protein related to gray leaf spot resistance, and an encoding gene and an application thereof.

BACKGROUND ART

Maize gray leaf spot (GLS) is a maize leaf disease that affects the yield and quality of maize. In the 1920s, gray leaf spot was first discovered in Alexandria County, Ill., USA. Later on, it gradually developed into a serious global plant leaf disease. Gray leaf spot is widely distributed in the main maize producing regions in the United States, Asia, Europe, and Africa. When the disease occurs, gray leaf spot can cause a 20-60% reduction in production. In the case of a severe disease, the reduction can reach 100%, causing serious economic losses to maize production.

Maize gray leaf spot is a fungal disease, and it is generally believed that the pathogenic fungi mainly include *Cercospora zeae-maydis* (Czm) and *Cercospora zeina* (Cz). In 2013, Liu et al. collected extensive disease samples from areas in China where maize gray leaf spot occurred, and obtained a large number of strains through the method of monospore isolation. By means of the methods of pathogen morphology, cultivation characteristic growth status, and molecular biology, they accurately identified the pathogenic species of maize gray leaf spot in different regions in China. *Cercospora zeae-maydis* is the cause of maize gray leaf spot disease in northern China, while *Cercospora zeina* is the cause of maize gray leaf spot disease in southwestern China.

According to reports, the resistance of maize to gray leaf spot belongs to quantitative inheritance, which is controlled by multiple genes with additive effects. In this regard, if the gray leaf spot resistance gene can be cloned and introduced into existing inbred lines using a molecular marker-assisted selection technology, this will be able to improve the gray leaf spot resistance of those popularized varieties.

SUMMARY OF THE INVENTION

The present invention provides a gray leaf spot resistance-related protein ZmWAK-RLK, and an encoding gene and an application thereof.

The protein provided by the present invention is obtained from the maize inbred line Y32 and named as ZmWAK-RLK protein, which is as follows: (a1), or (a2), or (a3), or (a4), or (a5):

(a1) a protein represented by SEQ ID NO: 1 in the sequence listing;

(a2) a protein represented by SEQ ID NO: 7 in the sequence listing;

(a3) a fusion protein obtained by attaching a tag to an N-terminus or/and a C-terminus of the protein of (a1) or (a2);

(a4) a protein related to plant gray leaf spot resistance obtained by substituting and/or deleting and/or adding one or a plurality of amino acid residues to the protein of (a1) or (a2); and (a5) a protein related to plant gray leaf spot resistance obtained from maize and having a homology of more than 90%, 91%, 92%, 93%, 94%, 95%, 96%, 97%, 98%, or 99% with the protein of (a1) or (a2).

The tags are as shown in Table 1 below.

TABLE 1

Tag sequences

| Tag | Residues | Sequence |
|---|---|---|
| Poly-Arg | 5 to 6 (typically 5) | RRRR (SEQ ID NO: 8) |
| Poly-His | 2 to 10 (typically 6) | HHHHHH (SEQ ID NO: 9) |
| FLAG | 8 | DYKDDDDK (SEQ ID NO: 10) |
| Strep-tag II | 8 | WSHPQFEK (SEQ ID NO: 11) |
| c-myc | 10 | EQKLISEEDL (SEQ ID NO: 12) |
| HA | 9 | YPYDVPDYA (SEQ ID NO: 13) |

The protein can be synthesized artificially, or its encoding gene can be synthesized first, and then the protein can be obtained by biological expression.

The nucleic acid molecule encoding the ZmWAK-RLK protein also falls within the scope of protection of the present invention.

The nucleic acid molecule is (b1), or (b2), or (b3), or (b4), or (b5), or (b6);

(b1) a DNA molecule with an encoding region that is represented by nucleotides 87 to 2084 in SEQ ID NO: 2 in the sequence listing;

(b2) a DNA molecule represented by SEQ ID NO: 2 in the sequence listing;

(b3) a DNA molecule represented by SEQ ID NO: 3 in the sequence listing;

(b4) a DNA molecule whose encoding region is represented by SEQ ID NO: 6 in the sequence listing;

(b5) a DNA molecule that is derived from maize, has a homology of more than 90%, 91%, 92%, 93%, 94%, 95%, 96%, 97%, 98%, or 99% with (b1), or (b2), or (b3), or (b4) and encodes the protein; and (b6) a DNA molecule that hybridizes to a nucleotide sequence defined by (b1), or (b2), or (b3), or (b4) under a stringent condition, and encodes the protein.

The stringent condition mentioned above is as follows: in a solution of 2×SSC, 0.1% SDS, hybridizing is performed at 68° C., the membrane is washed twice for 5 min each time, then hybridizing is performed again in a solution of 0.5×SSC, 0.1% SDS at 68° C., and the membrane is then washed twice for 15 min each time.

A DNA molecule, expression cassette, recombinant vector, or recombinant microorganism containing the nucleic acid molecule all falls within the scope of protection of the present invention.

The DNA molecule containing the nucleic acid molecule may specifically be as shown in Sequence 4 in the sequence listing.

Existing expression vectors can be used to construct a recombinant expression vector containing the nucleic acid molecule. When using the nucleic acid molecule to construct a recombinant expression vector, any enhanced, constitutive, tissue-specific, or inducible promoter can be added before its transcription initiation nucleotide, and they can be used alone or in combination with other plant promoters. In addition, when using the nucleic acid molecule to construct a recombinant expression vector, enhancers, including translation enhancers or transcription enhancers, can also be used. These enhancer regions can be ATG start codons or adjacent region start codons, but they must be in the same reading frame as the coding sequence in order to ensure correct translation of the entire sequence. The sources of the translation control signals and start codons are extensive, and they can be natural or synthetic. The translation initiation region can be derived from a transcription initiation region or a structural gene. In order to facilitate the identification and screening of transgenic plants or transgenic microorganisms, the expression vectors used can be processed. For example, genes expressing enzymes or luminescent compounds that can produce color changes in plants or microorganisms, resistant antibiotic markers, or chemical reagent resistant marker genes can be added herein. Considering the safety of the transgenes, it is possible to directly screen transformed plants or microorganisms by phenotype without adding any selectable marker genes.

The recombinant expression vector may specifically be a recombinant plasmid obtained by inserting the double-stranded DNA molecule shown in Sequence 4 in the sequence listing into the multiple cloning site (for example, the BamHI site) of the pCAMBIA3301 vector.

The recombinant expression vector may specifically be a recombinant plasmid obtained by inserting the double-stranded DNA molecule shown in nucleotides 87 to 2084 of Sequence 2 in the sequence listing into the multiple cloning site (for example, the Xcm I restriction site) of the pBCXUN vector.

The recombinant expression vector may specifically be a recombinant plasmid obtained by inserting the recombinant double-stranded DNA molecule shown in Sequence 6 in the sequence listing into the multiple cloning site (for example, the Xcm I restriction site) of the pBCXUN vector.

The present invention further sets forth an application of the ZmWAK-RLK protein, which is the following (c1), or (c2), or (c3), or (c4):

(c1) to regulate the resistance of a plant to gray leaf spot;

(c2) to increase the resistance of a plant to gray leaf spot;

(c3) to regulate the resistance of a plant to a disease caused by *Cercospora zeina;*

(c4) to increase the resistance of a plant to a disease caused by *Cercospora zeina.*

The present invention further sets forth an application of the nucleic acid molecule or the DNA molecule containing the nucleic acid molecule, which is the following (d1), or (d2), or (d3), or (d4):

(d1) to cultivate a transgenic plant with altered resistance to gray leaf spot;

(d2) to cultivate a transgenic plant with increased resistance to gray leaf spot;

(d3) to cultivate a transgenic plant with altered resistance to a disease caused by *Cercospora zeina;*

(d4) to cultivate a transgenic plant with increased resistance to a disease caused by *Cercospora zeina.*

The application of the nucleic acid molecule also includes an implementation method of using the gene through the CRISPS/CAS9 technology, for example, genome fragment reset (to introduce disease-resistant alleles into the susceptible genome), allele exchange (to replace susceptible alleles with disease-resistant alleles), changing susceptible alleles into disease-resistant alleles through gene editing, and so on.

The application of the nucleic acid molecule also includes other implementation methods aimed at enhancing the expression of the nucleic acid molecule. For example, the expression of the nucleic acid molecule can be increased by promoter replacement, the expression of the nucleic acid molecule can be increased by introducing an enhancer, and so on.

The present invention also sets forth a method for preparing a transgenic plant, which includes the following step: introducing the nucleic acid molecule or the DNA molecule containing the nucleic acid molecule into a starting plant to obtain a transgenic plant with increased resistant to gray leaf spot. The nucleic acid molecule can be specifically introduced into the starting plant through any one of the above-mentioned recombinant expression vectors. The recombinant expression vector carrying the nucleic acid molecule can be transformed into the starting plant by conventional biological methods such as Ti plasmid, Ri plasmid, plant virus vector, direct DNA transformation, microinjection, electrical conduction, and *agrobacterium* mediation. By crossing the transgenic plants with an existing maize variety (including single crosses and multiple crosses, such as three consecutive crosses), the obtained transgenic progeny plants are also transgenic plants with increased resistance to gray leaf spot. The existing maize variety may specifically be a maize inbred line Q11.

The present invention also sets forth a plant breeding method, which includes the following step: increasing the content and/or activity of the ZmWAK-RLK protein in a target plant, thereby increasing the resistance of the target plant to gray leaf spot.

The present invention also sets forth a method for preparing a transgenic plant, which includes the following step: introducing the nucleic acid molecule or the DNA molecule containing the nucleic acid molecule into a starting plant to obtain a transgenic plant with increased disease resistance; the disease resistance is the disease resistance to a disease caused by *Cercospora zeina*. The nucleic acid molecule can be specifically introduced into the starting plant through any one of the above-mentioned recombinant expression vectors. The recombinant expression vector carrying the nucleic acid molecule can be transformed into the starting plant by conventional biological methods such as Ti plasmid, Ri plasmid, plant virus vector, direct DNA transformation, microinjection, electrical conduction, and *agrobacterium* mediation. By crossing the transgenic plants with an existing maize variety (including single crosses and multiple crosses, such as three consecutive crosses), the obtained transgenic progeny plants are also transgenic plants with increased resistance to gray leaf spot. The existing maize variety may specifically be a maize inbred line Q11.

The present invention also sets forth a plant breeding method, which includes the following step: increasing the content and/or activity of the ZmWAK-RLK protein in a target plant, thereby increasing the disease resistance of the target plant; the disease resistance is the disease resistance to a disease caused by *Cercospora zeina*.

Any of the above-mentioned plants is a dicotyledonous plant or a monocotyledonous plant. The monocotyledonous plant may be a gramineous plant. The gramineous plant may be a plant of the genus *Zea*. The *Zea* plant may specifically be maize, such as maize inbred line B73 or maize inbred line B73-329.

Any of the above gray leaf spots may specifically be gray leaf spot caused by *Cercospora zeina*.

BRIEF DESCRIPTION OF THE DRAWINGS AND LEGENDS

FIG. 1 is the PCR identification results of some plants in Example 2. The arrow marks the target band (1197 bp). The leftmost lane is the molecular weight standard (M), each of the remaining lanes corresponds to a plant (numbered 1 to 18). If the 1197 bp amplification product is obtained, and the PCR identification is positive, the plant is a transgenic plant. If no amplification product is obtained, and the PCR identification is negative, the plant is a non-transgenic plant.

Figure 2:
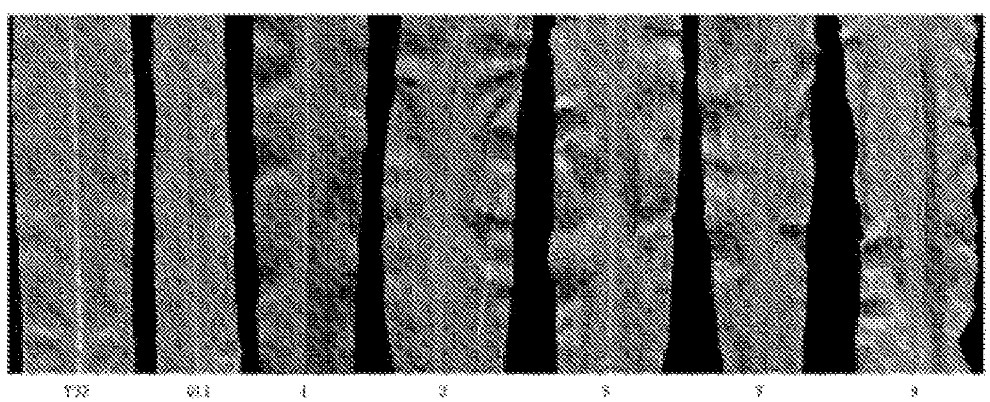

FIG. 2 is a photograph of representative leaves of each level; the disease-resistant parent Y32 has fewer disease spots on the leaves, while the susceptible parent Q11 has more disease spots on the leaves.

Figure 3:
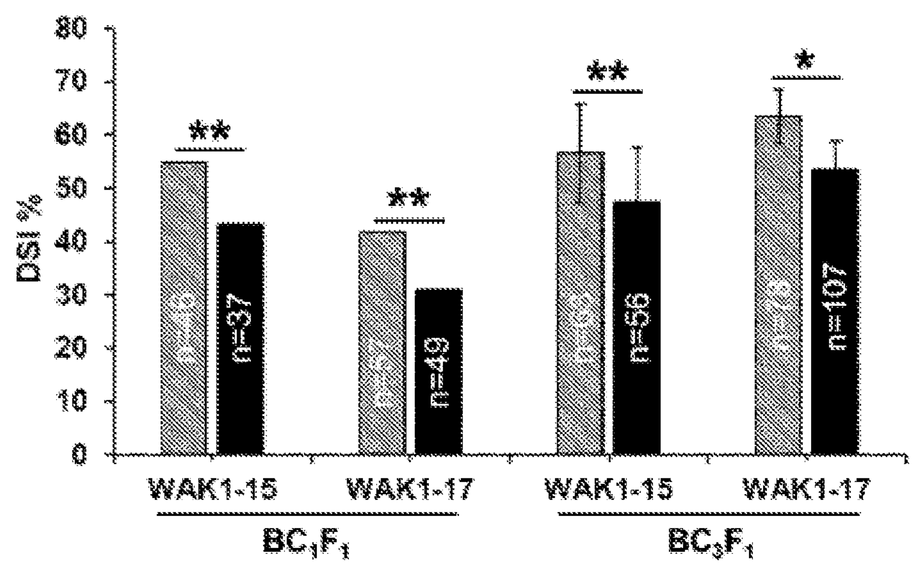

FIG. 3 is the results of the identification of disease resistance of the offspring separated from backcrossing in Example 2. In the $BC_1F_1$ generation and the $BC_3F_1$ generation, the disease index of the non-transgenic plants and that of the transgenic plants in the offspring of the two transgenic events WAK1-15 and WAK1-17 were counted respectively. The gray bars are non-transgenic plants, and the black bars are transgenic plants. The numbers in the bar graph indicate the numbers of plants. *: P<0.05; **: P<0.01.

Figure 4:
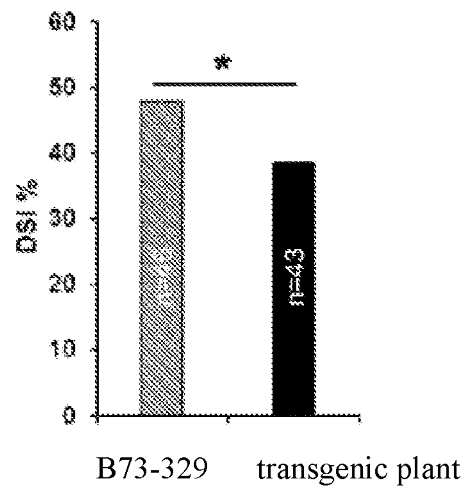

FIG. 4 is the results of the identification of disease resistance of the homozygous transgenic lines in Example 2. For the disease index of a homozygous transgenic positive plant and that of a transgenic receptor material (B73-329), it can be seen that the disease index of the homozygous transgene positive plant is significantly lower than that of the transgenic receptor material. The gray bar is B73-329, which is a transgenic receptor material. The black bar is a homozygous line of the transgenic plants. The numbers in the bar graph indicate the numbers of plants.

Figure 5:
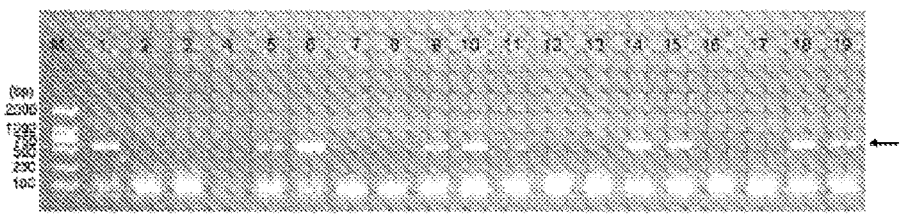

FIG. 5 is the PCR identification results of some plants in Example 3. The arrow marks the target band (530 bp). The leftmost lane is the molecular weight standard (M). Each of the remaining lanes corresponds to a plant (numbered 1 to 19). If the 530 bp amplification product is obtained, and the PCR identification is positive, the plant is a transgenic plant. If no amplification product is obtained, and the PCR identification is negative, the plant is a non-transgenic plant.

Figure 6:
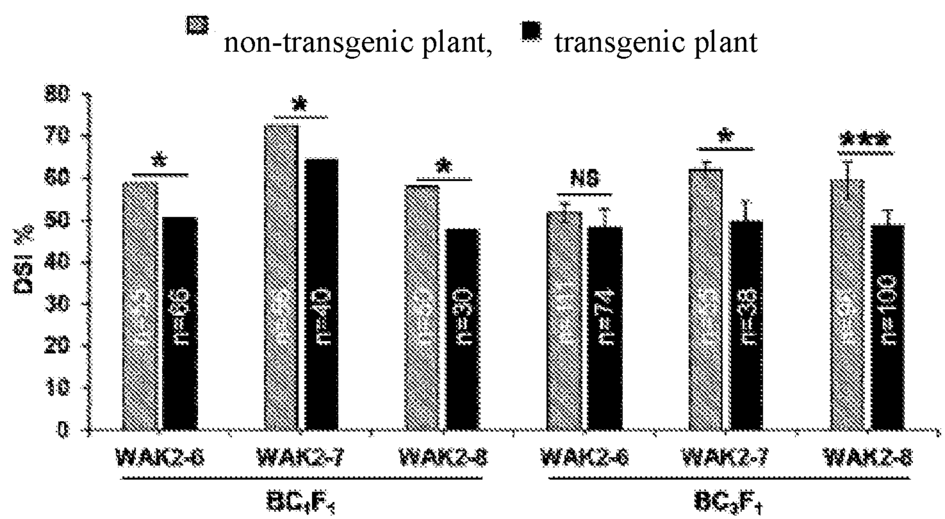

FIG. 6 is the results of the identification of disease resistance of the offspring separated from backcrossing in Example 3. In the $BC_1F_1$ generation and the $BC_3F_1$ generation, the disease index of the non-transgenic plants and that of the transgenic plants in the offspring of the three transgenic events WAK2-6, WAK2-7, and WAK2-8. The gray bars are non-transgenic plants; the black bars are transgenic plants. The numbers in the bar graph indicate the numbers of plants. *: P<0.05; ***: P<0.001; NS: No significant difference.

Figure 7:
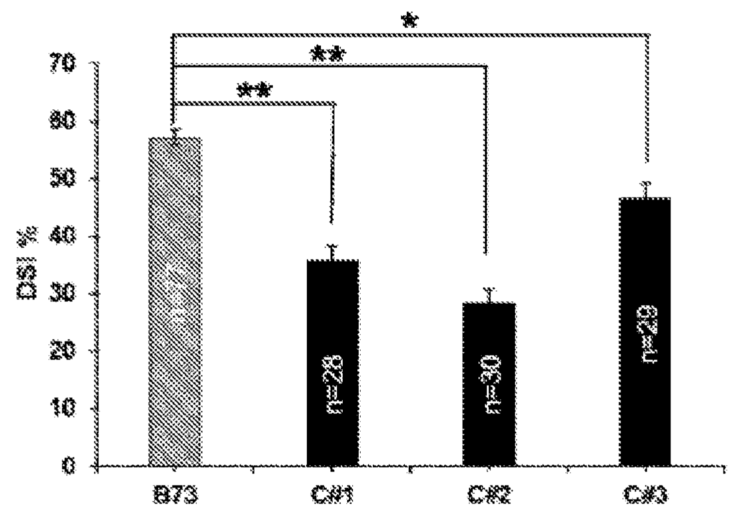

FIG. 7 is the disease resistance identification results (disease index) of the B73 background complementary transgenic homozygous lines in Example 4. The gray bar is B73, which is the transgenic receptor material. The black bars are the homozygous transgenic lines C #1, C #2, and C #3. The numbers in the bar graph indicate the numbers of plants. *: P<0.05; **: P<0.01.

Figure 8:
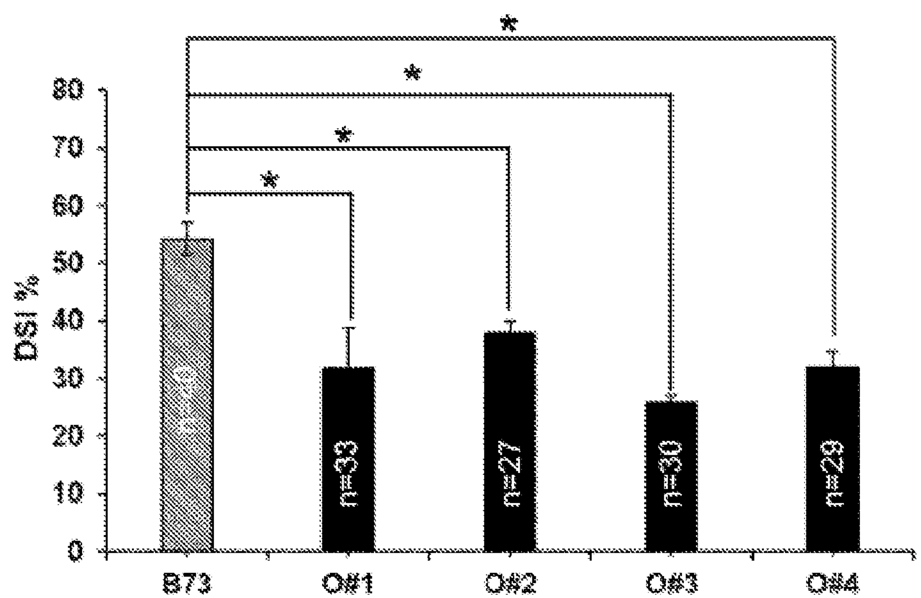

FIG. 8 is the disease resistance identification results (disease index) of the B73 background overexpression transgenic homozygous lines in Example 5. The gray bar is B73, which is the receptor material. The black bars are the homozygous transgenic lines O #1, O #2, O #3, and O #4. The numbers in the bar graph indicate the numbers of plants. *: P<0.05.

Figure 9:
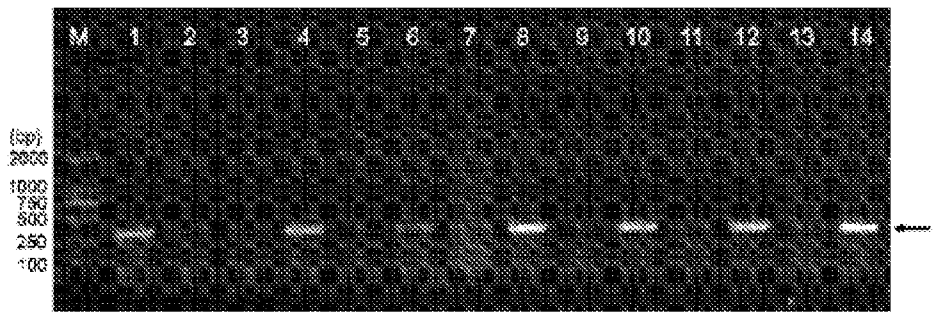

FIG. 9 is the PCR identification results of some plants in Example 6. The arrow marks the target band (357 bp). The leftmost lane is the molecular weight standard (M). Each of the remaining lanes corresponds to a plant (numbered 1 to 14). If the 357 bp amplification product is obtained, and the PCR identification is positive, the plant is a transgenic plant. If no amplification product is obtained, and the PCR identification is negative, the plant is a non-transgenic plant.

Figure 10:
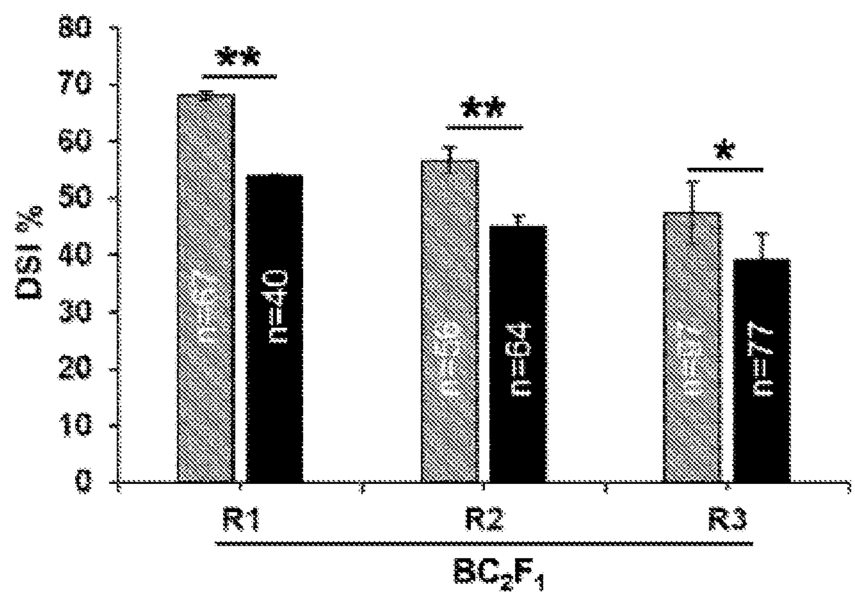

FIG. 10 is the disease resistance identification results (disease index) of the Q11 background chimeric gene overexpression plants in Example 6. In the $BC_2F_1$ generation, the disease index of the non-transgenic plants and that of the transgenic plants in the offspring of the three transgenic events of R1, R2, and R3 were counted. The gray bars are non-transgenic plants, and the black bars are transgenic plants. The numbers in the bar graph indicate the numbers of plants. *: P<0.05; **: P<0.01.

DESCRIPTION OF THE PREFERRED EMBODIMENTS

The following examples facilitate a better understanding of the present invention, but do not limit the present invention. The experimental methods in the following examples, unless otherwise specified, are all conventional methods. The experimental materials used in the following examples, unless otherwise specified, are all purchased from conventional biochemical reagent stores. The quantitative experiments in the following examples are all set to repeat the experiments three times, and the results are averaged.

The maize inbred line Y32 is a maize inbred line with high resistance to gray leaf spot of maize. The maize inbred line Y32 (line Y32) is described in the following literature: Theoretical and Applied Genetics, 2012, 25(8):1797-1808. Zhang, Y., et al. "QTL mapping of resistance to gray leaf spot in maize."

The maize inbred line Q11 is a maize inbred line highly susceptible to gray leaf spot. The maize inbred line Q11 (line Q11) is described in the following literature: Theoretical and Applied Genetics, 2012, 25(8):1797-1808. Zhang, Y., et al. "QTL mapping of resistance to gray leaf spot in maize."

The maize inbred line B73-329 (B73-329 inbred lines) is described in the following literature: New Phytologist, 2018, 217(3): 1161-1176. Zhang, M., et al. "A retrotransposon in an HKT1 family sodium transporter causes variation of leaf Na exclusion and salt tolerance in maize."

The maize inbred line B73 (B73 inbred lines) is described in the following literature: Plant Science, 1985, 41(2):140. Everett, N. P., et al. "Biochemical markers of embryogenesis in tissue cultures of the maize inbred B73."

*Cercospora zeina* is described in the following literature: Plant Disease, 2013, 97(12):1656-1656. Liu, K. J., et al. "First Report of Gray Leaf Spot of Maize Caused by *Cercospora zeina* in China."

The pCAMBIA3301 vector (bivalent expression vector pCAMBIA3301) is described in the following literature: Theoretical and Applied Genetics 131.10 (2018): 2145-2156. Zhu, X, et al. "Pyramiding of nine transgenes in maize generates high-level resistance against necrotrophic maize pathogens."

The pBCXUN vector is described in the following literature: Journal of integrative plant biology 61.6 (2019): 691-705. Qin, Y. J., et al. "ZmHAK5 and ZmHAK1 function in $K^+$ uptake and distribution in maize under low $K^+$ conditions."

Example 1 Discovery of ZmWAK-RLK Protein and an Encoding Gene Thereof

The maize inbred line Y32 with high resistance to gray leaf spot (as the donor parent) and the maize inbred line Q11 that is highly susceptible to gray leaf spot (as the recurrent parent) were used to construct the initial positioning population and the fine positioning population. In addition, qRgls1 was mapped between IDP2 and M2 of maize chromosome 8. The physical location is about 120 kb.

A finely positioned molecular marker located in the QTL-qRgls1 region was used, and the Y32 BAC library of the disease-resistant parents was screened by PCR. The BAC clone fingerprint analysis was used to construct BAC contigs covering the entire gene portion. The clones that could cover the least gene region were selected for sequencing. Through sequence alignment and expression analysis, a new gene was found, which encodes the protein shown in Sequence 1 in the sequence listing.

The protein shown in Sequence 1 in the sequence listing was named ZmWAK-RLK protein. The gene encoding the ZmWAK-RLK protein was named ZrnWAK-RLK gene. The ZrnWAK-RLK gene in the cDNA of the maize inbred line Y32 was shown in Sequence 2 in the sequence listing (where the nucleotides of 87 to 2084 are the open reading frame) (in Sequence 2, the nucleotides of 87 to 1058 are used for the construction of the chimeric gene). The ZmWAK-RLK gene in the genomic DNA of the maize inbred line Y32 was shown in Sequence 3 in the sequence listing. The open reading frame sequence of the ZrnWAK-RLK gene in the cDNA of the maize inbred line Q11 was shown in Sequence 5 in the sequence listing (in Sequence 5, the nucleotides of 1102 to 2115 were used to construct the chimeric gene). The chimeric gene was shown in Sequence 6 in the sequence listing, and expressed the chimeric protein shown in Sequence 7 in the sequence listing.

Example 2 Verifying the Function of a 7.2 kb Fragment

I. Obtaining Transgenic Plants

1. A fragment of about 7.2 kb in the maize inbred line Y32 (the fragment is shown in Sequence 4 in the sequence listing. In Sequence 4, the nucleotides 1 to 2103 were the promoter, and the nucleotides 2104 to 4316 were the same as Sequence 3 in the sequence listing) was inserted into the BamH I restriction site of the pCAMBIA3301 vector to obtain a recombinant plasmid.

2. The recombinant plasmid obtained in step 1 was introduced into *Agrobacterium* EHA105 to obtain a recombinant *Agrobacterium*.

3. The recombinant *Agrobacterium* obtained in step 2 was taken, and the *Agrobacterium* mediated method was used to genetically transform the immature embryos of the maize inbred line B73-329 to obtain T0 generation plants.

4. The T0 generation plants were selfed, the seeds were harvested, and the seeds were cultivated into plants, that is, the T1 generation plants.

5. The T1 generation plants were identified by PCR, and transgenic plants were screened. The transgenic plants selected from the T1 generation plants were the T1 transgenic plants. A number of transgenic plants were selected from the T1 generation plants, two of which were named WAK1-15 plant and WAK1-17 plant.

PCR identification method: plant leaves were taken, genomic DNA was extracted therefrom, and a primer pair composed of F1 and R1 was used for PCR amplification. If the 1197 bp amplification product was obtained, and the PCR identification was positive, the plant was a transgenic plant. If no amplification product was obtained, and the PCR identification was negative, the plant was a non-transgenic plant.

```
F1:
                                   (SEQ ID NO: 14)
CGAGGAGGTTTCCCGATATTAC;

R1:
                                   (SEQ ID NO: 15)
CACGTCAATCCGAAGGCTATTA.
```

FIG. 1 is the PCR identification results of some plants. The arrow marks the target band. The leftmost lane (M) is the molecular weight standard, and each of the remaining lanes (numbered 1 to 18) corresponds to a plant.

II. Obtaining B73-329 Genetic Background Transgenic Homozygous Line

The T1 transgenic plants were selfed and the seeds were harvested. The seeds were cultivated into plants, that is, the T2 generation plants. The T2 generation plants were selfed and the seeds were harvested. The seeds were cultivated into plants, that is, the T3 generation plants.

The T3 generation plants were identified by PCR (the PCR identification method was the same as 5 in step I).

For a T2 generation plant, if the T3 generation plants obtained by its selfing were all transgenic plants, this T2 generation plant was a homozygous transgenic plant. The offspring obtained by selfing of the homozygous transgenic plant were homozygous transgenic lines.

III. Obtaining the Offspring Separated from Backcrossing

The PCR identification method was the same as 5 in step I.

1. The WAK1-15 plant (or WAK1-17 plant) as the male parent was crossed with the maize inbred line Q11 as the female parent. The seeds were harvested, and cultivated into plants, that is, the $BC_1F_1$ plants. The transgenic plants and non-transgenic plants were identified and screened by PCR.

2. The WAK1-15 plant (or WAK1-17 plant) as the male parent was crossed with the maize inbred line Q11 as the female parent. The seeds were harvested, and cultivated into plants, that is, the $BC_1F_1$ plants. The transgenic plants were identified and screened by PCR. The transgenic plant of the $BC_1F_1$ plants was used as the male parent to cross with the maize inbred line Q11 as the female parent. The seeds were harvested, and cultivated into plants, that is, the $BC_2F_1$ plants. The transgenic plants were identified and screened by PCR. The transgenic plant of the $BC_2F_1$ plants was used as the male parent to cross with the maize inbred line Q11 as the female parent. The seeds were harvested, and cultivated into plants, that is, the $BC_3F_1$ plants. The transgenic plants and non-transgenic plants were identified and screened by PCR.

IV. Identifying Plant Disease Resistance

1. Methods of Identification of Disease Resistance

The disease resistance identification was carried out in Shangzhuang Experimental Base of China Agricultural University.

The pathogen of gray leaf spot: *Cercospora zeina.*

The plants as the experimental materials were cultivated under normal conditions, the pathogen was inoculated at the 10-leaf stage, and then the plants were cultivated again under the normal conditions. The phenotypic investigation was carried out two weeks after pollination. A graded survey was used to calculate the disease index (DSI). The specific method of inoculating the pathogen (method of pathogen solution infusion) was as follow: sterile water was used to suspend the spores of the pathogen of gray leaf spot to obtain a spore suspension with a spore concentration of $1\times10^5$ cfu/mL. A syringe was then used to infuse the spore suspension into the leaf heart of the maize plant, and 5 mL was used for each maize.

The grading standard of the disease levels (X represents the percentage of the diseased spot area to the leaf area):

Level 1 (assigned value was 0): X≤5%;

Level 3 (assigned value was 0.25): 5%<X≤10%;

Level 5 (assigned value was 0.5): 10%<X≤30%;

Level 7 (assigned value was 0.75): 30%<X≤70%;

Level 9 (assigned value was 1): 70%<X≤100%.

See FIG. 2 for photos of representative leaves of all levels.

Disease index (DSI) (%)=Σ(assigned value corresponding to a disease level×the number of plants at this level)×100/1×total number of plants 2. Identifying the Disease Resistance of the Offspring Separated from Backcrossing ($BC_1F_1$ Plants and $BC_3F_1$ Plants)

The first group of test materials: the transgenic plants and non-transgenic plants of the $BC_1F_1$ plants obtained with the WAK1-15 plant as the male parent as shown in 1 in step III, and the transgenic plants and non-transgenic plants of the $BC_1F_1$ plants obtained with the WAK1-17 plant as the male parent as shown in 1 in step III;

The second group of test materials: the transgenic plants and non-transgenic plants of the $BC_3F_1$ plants obtained with the WAK1-15 plant as the male parent as shown in 2 in step III, and the transgenic plants and non-transgenic plants of the $BC_3F_1$ plants obtained with the WAK1-17 plant as the male parent as shown in 2 in step III.

The first group of test materials was identified for disease resistance according to the method in step 1. The disease index of the transgenic plants was significantly lower than that of the non-transgenic plants, and DSI decreased by 10.5-11.6%.

The second group of test materials was identified for disease resistance according to the method in step 1. The disease index of the transgenic plants was significantly lower than that of the non-transgenic plants, and DSI decreased by 9.5-10.6%.

The results were shown in FIG. 3 (the gray bars are non-transgenic plants; the black bars are transgenic plants. The numbers in the bar graph indicate the numbers of plants. *: $P<0.05$; **: $P<0.01$.)

3. Identifying Disease Resistance of Homozygous Transgenic Lines

Test materials: T3 generation plants of the homozygous transgenic line obtained in step II and the maize inbred line B73-329 plants.

The test materials were identified for disease resistance according to the method in step 1. The results are shown in FIG. 4 (The gray bar is B73-329, which is the genetically modified receptor plant. The black bar is a homozygous line of the transgenic plants. The numbers in the bar graph indicate the numbers of plants. *: $P<0.05$). The disease index of transgenic plants was significantly lower than that of the maize inbred line B73-329 plants, and DSI was reduced by 9.5%.

The above results indicate that the ZmWAK-RLK gene is a functional gene of QTL-qRls1. Introducing the ZmWAK-RLK gene into maize can significantly reduce its gray leaf spot disease index by about 10%.

Example 3 Verifying the Function of the Open Reading Frame

I. Obtaining Transgenic Plants

1. The double-stranded DNA molecule shown as the nucleotides 87 to 2084 of Sequence 2 in the sequence listing was inserted into the Xcm I restriction site of the pBCXUN vector to obtain a recombinant plasmid.

2. The recombinant plasmid obtained in step 1 was introduced into *Agrobacterium* EHA105 to obtain a recombinant *Agrobacterium.*

3. The recombinant *Agrobacterium* obtained in step 2 was taken, and the *Agrobacterium* mediated method was used to genetically transform the immature embryos of the maize inbred line B73-329 to obtain T0 generation plants.

4. The T0 generation plants were selfed, and the seeds were harvested. The seeds were cultivated into plants, that is, the T1 generation plants.

5. The T1 generation plants were identified by PCR, and transgenic plants were screened. The transgenic plants selected from the T1 generation plants were the T1 transgenic plants. A number of transgenic plants were selected from the T1 generation plants, three of which were named WAK2-6 plant, WAK2-7 plant, and WAK2-8 plant.

PCR identification method: plant leaves were taken, genomic DNA was extracted therefrom, and a primer pair composed of F2 and R2 was used for PCR amplification. If the 530 bp amplification product was obtained, and the PCR identification was positive, the plant was a transgenic plant. If no amplification product was obtained, and the PCR identification was negative, the plant was a non-transgenic plant.

```
F2:
                                        (SEQ ID NO: 16)
TTTTAGCCCTGCCTTCATACGC;

R2:
                                        (SEQ ID NO: 17)
CGACATCGAATTCGGATAAAGGA.
```

The PCR identification results of some plants are shown in FIG. 5. The arrow marks the target band. The leftmost lane is the molecular weight standard (M). Each of the remaining lanes corresponds to a plant (numbered 1 to 19).

II. Obtaining the Offspring Separated from Backcrossing

The PCR identification method was the same as 5 in step I.

1. The WAK2-6 plant (or WAK2-7 plant or WAK2-8 plant) as the male parent was crossed with the maize inbred line Q11 as the female parent. The seeds were harvested, and cultivated into plants, that is, the $BC_1F_1$ plants. The transgenic plants and non-transgenic plants were identified and screened by PCR.

2. The WAK2-6 plant (or WAK2-7 plant or WAK2-8 plant) as the male parent was crossed with the maize inbred line Q11 as the female parent. The seeds were harvested, and cultivated into plants, that is, the $BC_1F_1$ plants. The transgenic plants were identified and screened by PCR. The transgenic plant of the $BC_1F_1$ plants was used as the male parent to cross with the maize inbred line Q11 as the female parent. The seeds were harvested, and cultivated into plants, that is, the $BC_2F_1$ plants. The transgenic plants were identified and screened by PCR. The transgenic plant of the $BC_2F_1$ plants was used as the male parent to cross with the maize inbred line Q11 as the female parent. The seeds were harvested, and cultivated into plants, that is, the $BC_3F_1$ plants. The transgenic plants and non-transgenic plants were identified and screened by PCR.

III. Identifying Plant Disease Resistance

1. Methods of Identification of Disease Resistance

The method was the same as 1 in step IV of Example 2.

2. Identifying the Disease Resistance of the Offspring Separated from Backcrossing ($BC_1F_1$ Plants and $BC_3F_1$ Plants)

The first group of test materials: the transgenic plants and non-transgenic plants of the $BC_1F_1$ plants obtained with the WAK2-6 plant as the male parent as shown in 1 in step II, the transgenic plants and non-transgenic plants of the $BC_1F_1$ plants obtained with the WAK2-7 plant as the male parent as shown in 1 in step II, and the transgenic plants and non-transgenic plants of the $BC_1F_1$ plants obtained with the WAK2-8 plant as the male parent as shown in 1 in step II;

The second group of test materials: the transgenic plants and non-transgenic plants of the $BC_3F_1$ plants obtained with the WAK2-6 plant as the male parent as shown in 2 in step II, the transgenic plants and non-transgenic plants of the $BC_3F_1$ plants obtained with the WAK2-7 plant as the male parent as shown in 2 in step II, and the transgenic plants and non-transgenic plants of the $BC_3F_1$ plants obtained with the WAK2-8 plant as the male parent as shown in 2 in step II.

The first group of test materials was identified for disease resistance according to the method in step 1. The disease index of the transgenic plants was significantly lower than that of the non-transgenic plants, and DSI decreased by 8.3-10.5%.

The second group of test materials was identified for disease resistance according to the method in step 1. The disease index of the transgenic plants was significantly lower than that of the non-transgenic plants, and DSI decreased by 10.8-11.9%.

The results were shown in FIG. 6 (the gray bars are non-transgenic plants, and the black bars are transgenic plants. The numbers in the bar graph indicate the numbers of plants. *: $P<0.05$; ***: $P<0.001$; NS: no significant difference).

The above results indicate that the ZmWAK-RLK gene is a functional gene in the main QTL-qRgls1 region for resistance to gray leaf spot. When it is backcrossed to be introduced to the Q11 genetic background, it can significantly improve the resistance of maize to gray leaf spot.

Example 4 Verifying the Function of the 7.2 kb Fragment on the B73 Genetic Background I. Obtaining Transgenic Plants 1. This step was the same as 1 in step I in Example 2.

2. This step was the same as 2 in step I in Example 2.

3. The recombinant *Agrobacterium* obtained in step 2 was taken, and the *Agrobacterium* mediated method was used to genetically transform the immature embryos of maize inbred line B73 to obtain the T0 generation plants.

4. The T0 generation plants were selfed, the seeds were harvested, and the seeds were cultivated into plants, that is, the T1 generation plants.

5. The T1 generation plants were identified by PCR, and transgenic plants were screened.

The PCR identification method was the same as 5 in Step I of Example 2.

The transgenic plants selected from the T1 generation plants were the T1 transgenic plants.

II. Obtaining Homozygous Transgenic Lines of B73 Genetic Background

The method was the same as step II of Example 2.

Three homozygous transgenic line materials were obtained, C #1 line, C #2 line, and C #3 line.

III. Identifying Plant Disease Resistance

1. Methods of Identification of Disease Resistance

The method was the same as 1 in step IV of Example 2.

2. Identifying Disease Resistance of Homozygous Transgenic Lines of the B73 Genetic Background Test materials: T3 generation plants of C #1 line, T3 generation plants of C #2 line, T3 generation plants of C #3 line, and maize inbred line B73 plants.

The test materials were identified for disease resistance according to the method in step 1.

Compared with the receptor material (maize inbred line B73 plants), the plant disease index of the C #1 line was significantly reduced (the reduction was 21.3%), the plant disease index of the C #2 line was significantly reduced (the reduction was 28.6%), and the plant disease index of the #3 line was also significantly reduced (the reduction was 10.5%). The results were shown in FIG. 7 (The gray bar is the transgenic receptor material, and the black bars are the homozygous transgenic plants. The numbers in the bar graph indicate the numbers of plants. *: $P<0.05$; **: $P<0.01$).

Overall, the transfer of the disease resistance gene ZmWAK-RLK can significantly reduce the disease index of maize gray leaf spot and increase the resistance of maize to gray leaf spot.

Example 5 Verifying the Function of the Open Reading Frame on the B73 Genetic Background

I. Obtaining Transgenic Plants

1. This step was the same as 1 in step I in Example 3.

2. This step was the same as 2 in step I in Example 3.

3. The recombinant *Agrobacterium* obtained in step 2 was taken, and the *Agrobacterium* mediated method was used to genetically transform the immature embryos of maize inbred line B73 to obtain the T0 generation plants.

4. The T0 generation plants were selfed, the seeds were harvested, and the seeds were cultivated into plants, that is, the T1 generation plants.

5. The T1 generation plants were identified by PCR, and transgenic plants were screened.

The PCR identification method was the same as 5 in Step I of Example 5.

The transgenic plants selected from the T1 generation plants were the T1 transgenic plants.

II. Obtaining Homozygous Transgenic Lines of B73 Genetic Background

The method was the same as step II of Example 2.

Four homozygous transgenic line materials were obtained, O #1 line, O #2 line, O #3 line, and O #4 line.

III. Identifying Plant Disease Resistance

1. Methods of Identification of Disease Resistance

The method was the same as 1 in step IV of Example 2.

2. Identifying Disease Resistance of Homozygous Transgenic Lines of the B73 Genetic Background Test materials: T3 generation plants of O #1 line, T3 generation plants of O #2 line, T3 generation plants of O #3 line, T3 generation plants of O #4 line, and maize inbred line B73 plants.

The test materials were identified for disease resistance according to the method in step 1.

Compared with the receptor material (maize inbred line B73 plants), the plant disease index of the O #1 line was significantly reduced (the reduction was 22.5%), the plant disease index of the O #2 line was significantly reduced (the reduction rate was 16.3%), the plant disease index of the O #3 line was significantly reduced (the reduction rate was 28.3%), and the plant disease index of the O #4 line was significantly reduced (the reduction rate was 22.2%). The results were shown in FIG. 8 (The gray bar is the transgenic recipient material, and the black bars are the homozygous transgenic plants. The numbers in the bar graph indicate the numbers of plants. *: $P<0.05$).

The results demonstrate that the ZmWAK-RLK gene is a functional gene in the main QTL-qRgls1 region for resistance to gray leaf spot, which can significantly improve the resistance of maize to gray leaf spot.

Example 6 Verifying the ZmWAK-RLK Functioning Section in Y32 on the Q11 Background

I. Obtaining Transgenic Plants

1. The double-stranded DNA molecule shown in Sequence 6 in the sequence listing was inserted into the Xcm I restriction site of the pBCXUN vector to obtain a recombinant plasmid.

2. The method was the same as 2 in step I of Example 3.

3. The recombinant *Agrobacterium* obtained in step 2 was taken, and the *Agrobacterium*-mediated method was used to genetically transform the immature embryos of maize inbred line B73 to obtain T0 generation plants.

4. The T0 generation plants were selfed, the seeds were harvested, and the seeds were cultivated into plants, that is, the T1 generation plants.

5. The T1 generation plants were identified by PCR, and transgenic plants were screened. The transgenic plants selected from the T1 generation plants were the T1 transgenic plants. A number of transgenic plants were selected from the T1 generation plants, three of which were named R1 plant, R2 plant, and R3 plant.

PCR identification method: plant leaves were taken, genomic DNA was extracted therefrom, and a primer pair composed of F3 and R3 was used for PCR amplification. If the 357 bp amplification product was obtained, and the PCR identification was positive, the plant was a transgenic plant. If no amplification product was obtained, and the PCR identification was negative, the plant was a non-transgenic plant.

```
F3:
                                   (SEQ ID NO: 18)
GGTGGACGGCGAGGTCGCCG;

R3:
                                   (SEQ ID NO: 19)
TCGGTGACGGGCAGGACCGG.
```

The PCR identification results of some plants are shown in FIG. 9. The arrow marks the target band. The leftmost lane is the molecular weight standard (M). Each of the remaining lanes corresponds to a plant (numbered 1 to 14).

II. Obtaining the Offspring Separated from Backcrossing

The PCR identification method was the same as 5 in step I.

The R1 plant (or R2 plant or R3 plant) as the male parent was crossed with the maize inbred line Q11 as the female parent. The seeds were harvested, and cultivated into plants, that is, the $BC_1F_1$ plants. The transgenic plants were identified and screened by PCR. The transgenic plant of the $BC_1F_1$ plants was used as the male parent to cross with the maize inbred line Q11 as the female parent. The seeds were harvested, and cultivated into plants, that is, the $BC_2F_1$ plants. The transgenic plants and non-transgenic plants were identified and screened by PCR.

III. Identifying Plant Disease Resistance

1. Methods of Identification of Disease Resistance

The method was the same as 1 in step IV of Example 2.

2. Identifying the Disease Resistance of the Offspring Separated from Backcrossing ($BC_2F_1$ Plants)

Test materials: the transgenic plants and non-transgenic plants of the $BC_2F_1$ plants obtained with the R1 plant as the male parent as shown in step II, the transgenic plants and non-transgenic plants of the $BC_2F_1$ plants obtained with the R2 plant as the male parent as shown in step II, and the transgenic plants and non-transgenic plants of the $BC_2F_1$ plants obtained with the R3 plant as the male parent as shown in step II;

The test materials were identified for disease resistance according to the method in step 1. The disease index of the transgenic plants was significantly lower than that of the non-transgenic plants, and DSI decreased by 8.4-14.1%.

The results were shown in FIG. 10 (the gray bars are non-transgenic plants, and the black bars are transgenic plants. The numbers in the bar graph indicate the number of plants. *: $P<0.05$; **: $P<0.01$).

The above results indicate that backcrossing the ZmWAK-RLK gene into the Q11 genetic background can significantly improve the resistance of maize to gray leaf spot. At the same time, it also shows that the N-terminal segment of ZmWAK-RLK protein (the amino acids 1 to 324 of Sequence 1 in the sequence listing) plays an important role in the resistance to gray leaf spot of maize.

INDUSTRIAL APPLICABILITY

The inventors of the present invention provide ZmWAK-RLK protein and its encoding gene. The experiments of overexpression of the transgene prove that the ZMWAK-RLK gene can increase the resistance of maize to gray leaf spot and significantly reduce the disease index of maize gray leaf spot. The present invention has great application value for the breeding of maize against gray leaf spot.

The invention claimed is:

1. A nucleic acid molecule, which encodes a protein comprising:

(i) the amino acid of SEQ ID NO: 1;

(ii) the amino acid of SEQ ID NO: 7;

(iii) the amino acid of SEQ ID NO: 1 or SEQ ID NO: 7 further comprising a peptide tag linked to an N-terminus or/and a C-terminus of SEQ ID NO: 1 or SEQ ID NO: 7; or (iv) an amino acid sequence that differs from SEQ ID NO: 1 or SEQ ID NO: 7 by a conservative substitution of one of the amino acid residues of SEQ ID NO: 1 or SEQ ID NO: 7;

wherein the nucleic acid molecule is operably linked to a heterologous promoter or a heterologous regulatory element.

2. The nucleic acid molecule according to claim 1, wherein the nucleic acid molecule comprises (bi) nucleotides 87 to 2084 of SEQ ID NO: 2;

(bii) SEQ ID NO: 2;

(biii) SEQ ID NO: 3; or (biv) SEQ ID NO: 6.

3. A DNA molecule, an expression cassette, a recombinant vector, or a recombinant microorganism comprising the nucleic acid molecule according to claim 2.

4. A method of enhancing the resistance of a plant to a disease caused by *Cercospora zeina*, optionally wherein the disease is gray leaf spot disease, said method comprising expressing a protein encoded by the nucleic acid molecule according to claim 1 in a transgenic plant.

5. The method according to claim 4, wherein the plant is a plant of the genus *Zea*.

6. The method according to claim 4 wherein said plant is transformed with a nucleic acid molecule, wherein the nucleic acid molecule encodes a protein comprising:

(i) the amino acid of SEQ ID NO: 1;

(ii) the amino acid of SEQ ID NO: 7;

(iii) the amino acid of SEQ ID NO: 1 or SEQ ID NO: 7 further comprising a peptide tag linked to an N-terminus or/and a C-terminus of SEQ ID NO: 1 or SEQ ID NO: 7; or (iv) an amino acid sequence that differs from SEQ ID NO: 1 or SEQ ID NO: 7 by a conservative substitution of one of the amino acid residues of SEQ ID NO: 1 or SEQ ID NO: 7.

7. The method according to claim 6, wherein said plant is a plant of the genus *Zea*.

8. A method for preparing a transgenic plant, comprising a step of: introducing the nucleic acid molecule according to claim 2 into a plant to obtain a transgenic plant with increased gray leaf spot resistance.

9. The method according to claim 8, wherein said plant is a plant of the genus *Zea*.

10. A plant breeding method, comprising the following step: crossing a transgenic plant having increased expression of a protein encoded by the nucleic acid molecule according to claim 1 with a target plant, thereby increasing the gray leaf spot resistance of the target plant.

11. The method according to claim 10, wherein the target plant is a plant of the genus *Zea*.

12. A method for preparing a transgenic plant, comprising a step of:

introducing the nucleic acid molecule of claim 2 into a starting plant to obtain a transgenic plant with increased disease resistance; the disease resistance being the resistance to a disease caused by *Cercospora zeina*.

13. The method according to claim 12, wherein the plant is a plant of the genus *Zea*.

14. A plant breeding method, comprising the following step: crossing a transgenic plant having increased expression of a protein encoded by the nucleic acid molecule according to claim 1 with a target plant, thereby increasing the gray leaf spot resistance of the target plant; the disease resistance being the resistance to a disease caused by *Cercospora zeina*.

15. The method according to claim 14, wherein the plant is a plant of the genus *Zea*.

* * * * *